(12) United States Patent
Schaper et al.

(10) Patent No.: US 6,281,221 B1
(45) Date of Patent: Aug. 28, 2001

(54) SUBSTITUTED 1,3-DIOXAN-5-YLAMINO-HEREROCYCLIC COMPOUNDS, PROCESSES FOR THEIR PREPARATION AND THEIR USE AS PEST CONTROL COMPOSITIONS

(75) Inventors: Wolfgang Schaper, Diedorf; Werner Knauf, Liederbach; Ulrich Sanft, Hofheim; Manfred Kern, Lörzweiler; Heinz Ehrhardt, Rehling; Adolf Heinz Linkies, Frankfurt; Dieter Bernd Reuschling, Butzbach; Werner Bonin, Kelkheim, all of (DE)

(73) Assignee: Hoechst Scering AgrEvo GmbH, Berlin (DE)

( * ) Notice: Subject to any disclaimer, the term of this patent is extended or adjusted under 35 U.S.C. 154(b) by 0 days.

(21) Appl. No.: 09/161,350

(22) Filed: Sep. 25, 1998

Related U.S. Application Data

(63) Continuation of application No. 08/671,540, filed on Jun. 27, 1996, now abandoned.

(51) Int. Cl.[7] .................. A01N 43/54; A61K 31/695; C07F 5/02; C07D 239/02; C07D 405/00
(52) U.S. Cl. .................. 514/259; 514/256; 514/336; 514/63; 544/229; 544/287; 544/326; 544/327; 544/328; 546/14; 546/256; 546/282.4
(58) Field of Search .................. 514/259, 256, 514/336, 63; 544/229, 287, 326, 327, 328; 546/14, 256, 282.4

(56) References Cited

U.S. PATENT DOCUMENTS

| | | | |
|---|---|---|---|
| 4,160,843 | 7/1979 | Szczepanski | 424/278 |
| 4,931,455 | 6/1990 | Yoshiora et al. | 544/327 |
| 5,124,333 | 6/1992 | Obata et al. | 544/327 |
| 5,571,815 | 11/1996 | Schaper et al. | 514/269 |
| 5,595,992 | 1/1997 | Preuss et al. | 514/254 |
| 5,650,417 | 7/1997 | Reuschling et al. | 54/345 |
| 5,668,140 | 9/1997 | Schaper et al. | 514/269 |
| 5,691,321 | 11/1997 | Schaper et al. | 514/256 |
| 5,723,450 | 3/1998 | Reuschling | 514/349 |
| 5,730,973 | 3/1998 | Morales et al. | 424/93.5 |

FOREIGN PATENT DOCUMENTS

| | | |
|---|---|---|
| 627 917 | 2/1982 | (CS) . |
| 42 08 254 | 9/1993 | (DE) . |
| 93-1774 | 11/1993 | (ZA) . |

OTHER PUBLICATIONS

Portnyagina et al., 1,3–Bis(mercaptopropyl)–2–thiopyrimidines. Chem. Heterocycl. pp. 557–561. (Khim. Geterotsikl. Soedin., 5, pp. 605–610.) (the English translation is sent), 1970.*

*Chemical Abstracts*, vol. 73, No. 17, Oct. 26, 1970, Abstract No. 87881s.

* cited by examiner

*Primary Examiner*—Richard L. Raymond
*Assistant Examiner*—Tamthom N. Truong
(74) *Attorney, Agent, or Firm*—Frommer Lawrence & Haug LLP

(57) ABSTRACT

The invention relates to novel substituted 1,3-dioxan-5-ylamino-heterocyclic compounds of the formula

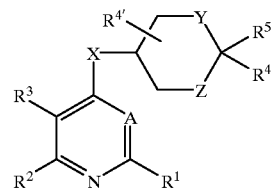

in which A is CH or N; X is NH, O or $S(O)_q$, where q=0–2; Y is O or $S(O)_m$, where m=0–2, and $R^1$, $R^2$, $R^3$, $R^4$, $R^{4'}$ and $R^5$ have the meanings given in the description, processes for their preparation and their use as pest control compositions and fungicides.

13 Claims, No Drawings

SUBSTITUTED 1,3-DIOXAN-5-YLAMINO-HEREROCYCLIC COMPOUNDS, PROCESSES FOR THEIR PREPARATION AND THEIR USE AS PEST CONTROL COMPOSITIONS

RELATED APPLICATION

This application is a continuation of application U.S. Ser. No. 08/671,540 filed Jun. 17, 1996 now abandoned which in turn claims priority to German application 195 23 906.7 filed Jun. 30, 1995, incorporated herein by reference.

FIELD OF THE INVENTION

The invention relates to novel substituted 1,3-dioxan-5-ylamino-heterocyclic compounds, processes for their preparation and their use as pest control compositions and fungicides.

BACKGROUND OF THE INVENTION

It is already known that certain cycloamino- and -alkoxy-heterocyclic compounds show a fungicidal, acaricidal and insecticidal action (DE-A-42 08 254, incorporated herein by reference). However, the biological action of these compounds is not satisfactory in all examples of use, especially when low amounts are applied and at low concentrations.

SUMMARY OF THE INVENTION

Novel 1,3-dioxan-5-ylamino-heterocyclic compounds have been found of the formula I

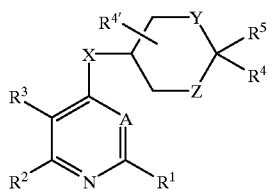

in which the radicals and groups are as defined below.

OBJECTS OF THE INVENTION

The invention provides compounds which have a very good plant tolerance and favourable toxicity with respect to warm-blooded animals and are particularly suitable for control of animal pests, such as insects, arachnids, nematodes, helminths and mollusks, for control of endo- and ectoparasites in the veterinary medicine field and for control of harmful fungi.

The foregoing and other objects and advantages of the invention will be set forth in or apparent from the following description.

The invention therefore relates to compounds of the formula I in which $R^1$ is hydrogen, halogen, $(C_1-C_4)$-alkyl, $(C_1-C_4)$-haloalkyl or $(C_3-C_5)$-cycloalkyl;

$R^2$ and $R^3$ are identical or different and are each hydrogen, $(C_1-C_4)$-alkyl, $(C_1-C_4)$-haloalkyl, $(C_2-C_4)$-alkenyl, $(C_2-C_4)$-haloalkenyl, $(C_2-C_4)$-alkynyl, $(C_2-C_4)$-haloalkynyl, $(C_1-C_8)$-trialkylsilylalkynyl, preferably dimethyl-$(C_1-C_8)$-alkyl-silyl-alkynyl, phenyl-$(C_1-C_8)$-dialkyl-silyl-alkynyl, preferably phenyl-dimethyl-silyl-alkynyl, aryl-$(C_1-C_2)$-alkyl-$(C_1-C_8)$-dialkyl-silyl-alkynyl, preferably benzyl-dimethyl-silyl-alkynyl, $(C_3-C_8)$-cycloalkyl-$(C_1-C_8)$-dialkyl-silyl-alkynyl, preferably $(C_3-C_8)$-cycloalkyl-dimethyl-silyl-alkynyl, (1-methyl-sila-$(C_3-C_8)$-cycloalkyl-1-yl)-alkynyl, preferably (1-methyl-silacyclopent-1-yl)-alkynyl or (1-methyl-sila-cyclohex-1-yl)-alkynyl, triphenylsilylalkynyl, $(C_1-C_4)$-alkoxy, $(C_1-C_4)$-haloalkoxy, $(C_1-C_4)$-alkoxy-$(C_1-C_4)$-alkyl, $(C_1-C_4)$-haloalkoxy-$(C_1-C_4)$-alkyl, $(C_1-C_4)$-alkoxy-$(C_1-C_4)$-haloalkyl, $(C_1-C_4)$-haloalkoxy-$(C_1-C_4)$-haloalkyl, halogen, hydroxyl, $(C_1-C_4)$-hydroxyalkyl, $(C_1-C_4)$-alkanoyl, $(C_1-C_4)$-alkanoyl-$(C_1-C_4)$-alkyl, $(C_1-C_4)$-haloalkanoyl, $(C_3-C_5)$-cyclo-alkyl, $(C_3-C_5)$-halocycloalkyl, cyano, $(C_1-C_4)$-cyanoalkyl, nitro, $(C_1-C_4)$-nitroalkyl, thiocyano, $(C_1-C_4)$-thiocyanoalkyl, $(C_1-C_4)$-alkoxycarbonyl, $(C_1-C_4)$-alkoxycarbonyl-$(C_1-C_4)$-alkyl, $(C_1-C_4)$-haloalkoxycarbonyl, $(C_1-C_4)$-alkylthio, $(C_1-C_4)$-alkylthio-$(C_1-C_4)$-alkyl, $(C_1-C_4)$-haloalkylthio, $(C_1-C_4)$-alkyl-sulfinyl, $(C_1-C_4)$-haloalkylsulfinyl, $(C_1-C_4)$-alkylsulfonyl or $(C_1-C_4)$-haloalkylsulfonyl; or $R^2$ and $R^3$, together with the carbon atoms to which they are bonded, form an unsaturated 5- or 6-membered isocyclic ring which, if it is a 5-membered ring, can contain one oxygen or sulfur atom instead of $CH_2$ or which, if it is a 6-membered ring, can contain one or two nitrogen atoms instead of one or two CH units, and which is optionally substituted by 1, 2 or 3 identical or different radicals, and these radicals are $(C_1-C_4)$-alkyl, $(C_1-C_4)$-haloalkyl, preferably trifluoromethyl, halogen, $(C_1-C_4)$-alkoxy or $(C_1-C_4)$-haloalkoxy; or $R^2$ and $R^3$, together with the carbon atoms to which they are bonded, form a saturated 5-, 6- or 7-membered isocyclic ring which can contain oxygen and/or sulfur instead of one or two $CH_2$ groups, and which is optionally substituted by 1, 2 or 3 $(C_1-C_4)$-alkyl groups;

A is CH or N;

X is NH, oxygen or $S(O)_q$, where q=0, 1 or 2;

Y and Z are oxygen or a group $S(O)_m$, where m=0, 1 or 2;

$R^4$, $R^{4'}$ and $R^5$ are substituents of the heteroaliphatic ring system;

$R^4$ and $R^{4'}$ are hydrogen, halogen, $(C_1-C_4)$-alkyl, $(C_1-C_4)$-haloalkyl, $(C_1-C_4)$-alkoxy or $(C_1-C_4)$-alkylthio;

$R^5$ is alkyl, alkenyl, alkynyl, aryl or heterocyclyl, where the aryl or heterocyclyl radicals mentioned can be unsubstituted or provided with up to three, in the case of fluorine also up to the maximum number of, identical or different radicals, and in the alkyl, alkenyl or alkynyl radicals mentioned, one or more, preferably up to three, non-adjacent saturated carbon units can be replaced by a carbonyl group or by heteroatom units, such as oxygen, $S(O)_x$, where x=0, 1 or 2, $NR^6$ or $SiR^7R^8$, in which $R^6$ is hydrogen, $(C_1-C_4)$-alkyl, $(C_1-C_4)$-alkoxy or $(C_1-C_4)$-alkanoyl and $R^7$ and $R^8$ are $(C_1-C_4)$-alkyl, preferably methyl; and wherein, furthermore, 3 to 12 atoms of these hydrocarbon radicals optionally modified as above can form a ring, and these hydrocarbon radicals, with or without the variations mentioned, can optionally be substituted by one or more, preferably up to three, in the case of fluorine up to the maximum number of, identical or different radicals from the series consisting of halogen, aryl, aryloxy, arylthio, cycloalkoxy, cycloalkylthio, heterocyclyl, heterocyclyloxy, heterocyclylthio, alkanoyl, cycloalkanoyl, haloalkanoyl, aroyl, arylalkanoyl, cycloalkylalkanoyl, heterocyclylalkanoyl, alkoxycarbonyl, haloalkoxycarbonyl, cycloalkoxycarbonyl, cycloalkylalkoxycarbonyl, arylalkoxycarbonyl, heterocyclylalkoxycarbonyl, aryloxycarbonyl, heterocyclyloxycarbonyl, alkanoyloxy, haloalkanoyloxy, cycloalkanoyloxy, cycloalkylalkanoyloxy, aroyloxy, arylalkanoyloxy, heterocycloylalkanoyloxy, alkyl-sulfonyloxy, arylsulfonyloxy, hydroxyl, cyano, thiocyano and nitro, where the cycloaliphatic, aromatic or heterocyclic ring systems among the substituents just mentioned can be unsubstituted or provided with up to three, in the case of fluorine also up to the maximum number of, identical or different substituents, or $R^4$ and $R^5$ together form a three- to eight-membered ring system which is linked spirocyclically to the ring system containing the heteroatoms Y and Z and in which one or two $CH_2$ groups, preferably one $CH_2$ group, can be replaced by heteroatom units, such as oxygen, $S(O)_n$, where n=0, 1 or 2, or $NR^9$, in which $R^9$ is hydrogen, alkyl, alkoxy, alkanoyl, benzoyl, aryl or heteroaryl, where the benzoyl, aryl or heteroaryl radicals can be unsubstituted or provided with up to three, in the case of fluorine also up to the maximum number of, identical or different substituents, and the ring system formed from $R^4$ and $R^5$ can be unsubstituted or provided with up to three, but preferably one, substituent(s), and these substituents are identical or different and are in each case alkyl, haloalkyl, alkoxy, alkylthio, aryl, aryloxy, arylthio, arylalkyl, arylalkoxy, arylalkylthio, cycloalkyl, cycloalkoxy, cycloalkylthio, heterocyclyl, heterocyclyloxy, heterocyclylthio, trialkylsilyl or alkoxycarbonyl, where the cycloaliphatic, aromatic or heterocyclic ring systems among the substituents just mentioned can be unsubstituted or provided with up to three, in the case of fluorine also up to the maximum number of, identical or different substituents, or the ring system formed from $R^4$ and $R^5$, together with a further benzene ring or cyclohexane ring, forms a fused ring system, preferably the indane, 1,2,3,4-tetrahydronaphthalene, dekalin or benzocycloheptane system, and the benzene ring in these fused systems can be unsubstituted or provided with up to three, in the case of fluorine also up to the maximum number of, identical or different substituents, and salts thereof, preferably acid addition salts; in particular those compounds for which $R^5$ is $(C_1-C_{20})$-alkyl, $(C_2-C_{20})$-alkenyl, $(C_2-C_{20})$-alkynyl, aryl or heterocyclyl, where the aryl or heterocyclyl radicals mentioned can be unsubstituted or provided with up to three, in the case of fluorine also up to the maximum number of, identical or different radicals, and in the alkyl, alkenyl or alkynyl radicals mentioned, one or more, preferably up to three, non-adjacent saturated carbon units can be replaced by a carbonyl group or by heteroatom units, such as oxygen, $S(O)_x$, where x=0, 1 or 2, $NR^6$ or $SiR^7R^8$, in which $R^6$ is hydrogen, $(C_1-C_4)$-alkyl, $(C_1-C_4)$-alkoxy or $(C_1-C_4)$-alkanoyl and $R^7$ and $R^8$ are $(C_1-C_4)$-alkyl, preferably methyl, and wherein, furthermore, 3 to 12 atoms of these hydrocarbon radicals optionally modified as above can form a ring, and these hydrocarbon radicals, with or without the variations mentioned, can optionally be substituted by one or more, preferably up to three, in the case of halogen up to the maximum number of, identical or different radicals from the series consisting of halogen, aryl, aryloxy, arylthio, $(C_3-C_8)$-cycloalkoxy, $(C_3-C_8)$-cycloalkylthio, heterocyclyl, heterocyclyloxy, heterocyclylthio, $(C_1-C_{12})$-alkanoyl, $(C_3-C_8)$-cycloalkanoyl, $(C_2-C_{12})$-haloalkanoyl, aroyl, aryl-$(C_1-C_4)$-alkanoyl, $(C_3-C_8)$-cycloalkyl-$(C_1-C_4)$-alkanoyl, heterocyclyl-$(C_1-C_4)$-alkanoyl, $(C_1-C_{12})$-alkoxycarbonyl, $(C_1-C_{12})$-haloalkoxycarbonyl, $(C_3-C_8)$-cycloalkoxycarbonyl, $(C_3-C_8)$-cycloalkyl-$(C_1-C_4)$-alkoxycarbonyl, aryl-$(C_1-C_4)$-alkoxycarbonyl, heterocyclyl-$(C_1-C_4)$-alkoxycarbonyl, aryloxycarbonyl, heterocyclyloxycarbonyl, $(C_1-C_{12})$-alkanoyloxy, $(C_2-C_{12})$-haloalkanoylalkoxy, $(C_3-C_8)$-cycloalkanoyloxy, $(C_3-C_8)$-cycloalkyl-$(C_1-C_4)$-alkanoyloxy, aroyloxy, aryl-$(C_1-C_4)$-alkanoyloxy, heterocyclyl-$(C_1-C_4)$-alkanoyloxy, $(C_1-C_{12})$-alkylsulfonyloxy, arylsulfonyloxy, hydroxyl, cyano, thiocyano and nitro, where the cycloaliphatic, aromatic or heterocyclic ring systems among the substituents just mentioned can be unsubstituted or provided with up to three, in the case of fluorine also up to the maximum number of, identical or different substituents, or $R^4$ and $R^5$ together form a three- to eight-membered ring system which is linked spirocyclically to the ring system containing the heteroatoms Y and Z, and in which one or two $CH_2$ groups, preferably one $CH_2$ group, can be replaced by heteroatom units, such as oxygen, $S(O)_n$, where n=0, 1 or 2, or $NR^9$, in which $R^9$ is hydrogen, $(C_1-C_8)$-alkyl, $(C_1-C_8)$-alkoxy, $(C_1-C_8)$-alkanoyl, benzoyl, aryl or heteroaryl, where the benzoyl, aryl or heteroaryl radicals can be unsubstituted or provided with up to three, in the case of fluorine also up to the maximum number of, identical or different substituents, and the ring system formed from $R^4$ and $R^5$ can be unsubstituted or provided with up to three, but preferably one, substituent(s), and these substituents are identical or different and are in each case $(C_1-C_8)$-alkyl, $(C_1-C_8)$-haloalkyl, $(C_1-C_8)$-alkoxy, $(C_1-C_8)$-alkylthio, $(C_3-C_8)$-cycloalkyl, $(C_3-C_8)$-cycloalkoxy, $(C_3-C_8)$-cycloalkylthio, aryl, aryloxy, arylthio, aryl-$(C_1-C_4)$-alkyl, aryl-$(C_1-C_4)$-alkoxy, aryl-$(C_1-C_4)$-alkylthio, heterocyclyl, heterocyclyloxy, heterocyclylthio, $(C_1-C_8)$-trialkylsilyl, preferably $(C_1-C_8)$-alkyl-dimethylsilyl or $(C_1-C_8)$-alkoxycarbonyl, where the cycloaliphatic, aromatic or heterocyclic ring systems among the substituents just mentioned can be unsubstituted or provided with up to three, in the case of fluorine also up to the maximum number of, identical or different substituents, or the ring system formed from $R^4$ and $R^5$, together with a further benzene ring or cyclohexane ring, forms a fused ring system, preferably the indane, 1,2,3,4-tetrahydronaphthalene, decahydronaphthalene or benzocycloheptane system, and the benzene ring in these fused systems can be unsubstituted or provided with up to three, in the case of fluorine also up to the maximum number of, identical or different substituents, and where, among the compounds for which the carbon atom between the heteroatoms Y and Z carries only the substituent $R^5$, the substituents X and $R^5$ are preferably in the cis-position relative to one another.

DESCRIPTION OF THE PREFERRED EMBODIMENTS

Preferred compounds of the formula I are those in which $R^1$ is hydrogen or fluorine;

$R^2$ and $R^3$ are hydrogen, $(C_1-C_4)$-alkyl, $(C_2-C_4)$-alkenyl, $(C_2-C_4)$-alkynyl, trimethylsilylethynyl, methoxycarbonyl, $(C_1-C_4)$-haloalkyl, halogen, methoxymethyl or cyano; or $R^2$ and $R^3$, together with the carbon atoms to which they are bonded, form an optionally substituted unsaturated 5- or 6-membered ring which, in the case of the 5-membered ring, can contain one sulfur atom instead of one $CH_2$ unit; or $R^2$ and $R^3$, together with the carbon atoms to which they are bonded, form a saturated 5- or 6-membered ring which can contain one sulfur or one oxygen atom instead of one $CH_2$ unit;

A is CH or N;

X is NH or oxygen;

Y and Z are each oxygen or sulfur;

$R^4$ is hydrogen, $(C_1-C_4)$-alkyl, trifluoromethyl or $(C_1-C_4)$-alkoxy;

$R^{4'}$ is hydrogen;

in particular those compounds in which $R^1$ is hydrogen, $R^2$ and $R^3$ are hydrogen, methyl, ethyl, propyl, $(C_2-C_3)$-alkenyl, $(C_2-C_3)$-chloro- or fluoro-alkenyl, $(C_2-C_3)$-alkynyl, trimethylsilylethynyl, $(C_1-C_3)$-chloro- or fluoroalkyl, methoxymethyl, halogen or cyano;

$R^2$ and $R^3$, together with the ring system to which they are bonded, form the quinazoline or quinoline system which can be substituted by fluorine in the carbocyclic part; or $R^2$ and $R^3$, together with the carbon atoms to which they are bonded, form a saturated 6-membered ring which can contain one oxygen or sulfur atom instead of one $CH_2$ group;

$R^4$ is hydrogen or methyl;

$R^{4'}$ is hydrogen.

Particularly preferred compounds of the formula I are those in which $R^1$ is hydrogen;

$R^2$ is methyl, ethyl, propyl, isopropyl, vinyl, ethynyl, $(C_1-C_2)$-fluoroalkyl or methoxymethyl;

$R^3$ is fluorine, chlorine, bromine, cyano, vinyl, ethynyl, $(C_1-C_2)$-fluoroalkyl or methoxy; or in the case where A is nitrogen, $R^2$ and $R^3$, together with the ring system to which they are bonded, form the quinazoline system which can be substituted by a fluorine atom;

A is CH or N;

X is NH;

Y and Z are oxygen or sulfur;

$R^4$ and $R^{4'}$ are hydrogen.

Compounds of the formula I which are most preferred are those in which $R^1$ is hydrogen;

$R^2$ is ethyl or methoxymethyl;

$R^3$ is chlorine, bromine or methoxy, preferably those for which $R^2$ is ethyl and $R^3$ is chlorine;

A is nitrogen;

X is NH;

Y and Z are oxygen;

$R^4$ and $R^{4'}$ are hydrogen;

$R^5$ is $(C_1-C_{20})$-alkyl, $(C_2-C_{20})$-alkenyl, $(C_2-C_{20})$-alkynyl, aryl or heterocyclyl, where the aryl or heterocyclyl radicals mentioned can be unsubstituted or provided with up to three, in the case of fluorine also up to the maximum number of, identical or different radicals, and in the alkyl, alkenyl or alkynyl radicals mentioned, one or more, preferably up to three, non-adjacent saturated carbon units can be replaced by heteroatom units, such as oxygen or $SiR^7R^8$, in which $R^7$ and $R^8$ are $(C_1-C_4)$-alkyl, preferably methyl, and wherein, furthermore, 3 to 6 atoms of these hydrocarbon radicals optionally modified as above can form a ring, and these hydrocarbon radicals, with or without the variations mentioned, can optionally be substituted by one or more, preferably up to three, in the case of halogen up to the maximum number of, identical or different radicals from the series consisting of halogen, preferably fluorine, aryl, aryloxy, arylthio, $(C_3-C_8)$-cycloalkoxy, $(C_3-C_8)$-cycloalkylthio, heterocyclyl, heterocyclyloxy and $(C_1-C_2)$-alkoxycarbonyl, where the cycloaliphatic, aromatic or heterocyclic ring systems among the substituents just mentioned can be unsubstituted or provided with up to three, in the case of fluorine also up to the maximum number of, identical or different substituents, or $R^4$ and $R^5$ together form a five- or six-membered ring system which is preferably linked spirocyclically to the ring system containing the heteroatoms Y and Z, and in which one $CH_2$ group can be replaced by heteroatom units, such as oxygen, $S(O)_n$, where n=0, 1 or 2, or $NR^9$, in which $R^9$ is hydrogen, $(C_1-C_8)$-alkyl, $(C_1-C_8)$-alkanoyl, benzoyl, aryl or heteroaryl, where the benzoyl, aryl or heteroaryl radicals can be unsubstituted or provided with up to three, in the case of fluorine also up to the maximum number of, identical or different substituents, and the ring system formed from $R^4$ and $R^5$ can be unsubstituted or provided with up to three, but preferably one, substituent(s), and these substituents are identical or different and are in each case $(C_1-C_8)$-alkyl, $(C_3-C_8)$-cycloalkyl, aryl or aryl-$(C_1-C_4)$-alkyl, where the cycloaliphatic, aromatic or heterocyclic ring systems among the substituents just mentioned can be unsubstituted or provided with up to three, in the case of fluorine also up to the maximum number of, identical or different substituents, or the ring system formed from $R^4$ and $R^5$, together with a further benzene ring or cyclohexane ring, forms a fused ring system, preferably the indane, 1,2,3,4-tetrahydronaphthalene, dekalin or benzocycloheptane system, and the benzene ring in these fused systems can be unsubstituted or provided with up to three, in the case of fluorine also up to the maximum number of, identical or different substituents, and where, among the compounds for which the carbon atom between the heteroatoms Y and Z carries only the substituent $R^5$, the substituents X and $R^5$ on the heteroaliphatic six-membered ring are preferably in the cis-position relative to one another;

in particular those compounds for which $R^5$ is $(C_1-C_{15})$-alkyl, aryl or heterocyclyl in the sense of a heteroaromatic ring system, where the aryl or heterocyclyl radical can be unsubstituted or provided with up to three, in the case of fluorine also up to the maximum number of, identical or different radicals, and in the alkyl radical mentioned, one or more, preferably up to three, non-adjacent saturated carbon units can be replaced by oxygen, and wherein, furthermore, 3 to 8 atoms of this alkyl radical optionally modified as above can form a ring, and this alkyl radical, with or without the variations mentioned, can optionally be substituted by one or more halogen atoms, in the case of fluorine also up to the maximum number, or by an aryl radical, and this aryl radical can be unsubstituted or provided with up to three, in the case of fluorine also up to the maximum number of, identical or different substituents, and the substituents X and $R^5$ on the heteroaliphatic six-membered ring are preferably in the cis-position relative to one another.

In the above formula, "halogen" is to be understood as meaning a fluorine, chlorine, bromine or iodine atom;

the term "$(C_1–C_4)$-alkyl" is to be understood as meaning an unbranched or branched hydrocarbon radical having 1 to 4 carbon atoms, such as, for example, the methyl, ethyl, propyl, isopropyl, 1-butyl-, 2-butyl-, 2-methylpropyl- or tert-butyl radical;

the term "$(C_1–C_8)$-alkyl" is to be understood as meaning the above mentioned alkyl radicals and, for example, the pentyl, 2-methylbutyl, 1,1-dimethylpropyl, hexyl, heptyl, octyl or the 1,1,3,3-tetramethylbutyl radical;

the term "$(C_1–C_{20})$-alkyl" is to be understood as meaning the abovementioned alkyl radicals and, for example, the nonyl, 1-decyl, 2-decyl, undecyl, dodecyl, pentadecyl or eicosyl radical; the term "$(C_1–C_4)$-haloalkyl" is to be understood as meaning an alkyl group mentioned under the term "$(C_1–C_4)$-alkyl" in which one or more hydrogen atoms are replaced by the abovementioned halogen atoms, preferably chlorine or fluorine, such as, for example, the trifluoromethyl group, the 1-fluoroethyl group, the 2,2,2-trifluoroethyl group, the chloromethyl or fluoromethyl group, the difluoromethyl group or the 1,1,2,2-tetrafluoroethyl group;

the term "$(C_1–C_2)$-fluoroalkyl" is to be understood as meaning, for example, the mono-, di- or trifluoromethyl group or the 1-fluoroethyl, 2-fluoroethyl, 1,1-difluoroethyl, 2,2,2-trifluoroethyl or pentafluoroethyl group;

the term "cycloalkyl" is to be understood as meaning preferably $(C_3–C_8)$-cycloalkyl;

the term "cycloalkoxy" is to be understood as meaning preferably $(C_3–C_8)$-cycloalkoxy;

the term "cycloalkylthio" is to be understood as meaning preferably $(C_3–C_8)$-cycloalkylthio;

the term "$(C_3–C_5)$-cycloalkyl" is to be understood as meaning the cyclopropyl, cyclobutyl or cyclopentyl group;

the term "$(C_3–C_8)$-cycloalkyl" is to be understood as meaning the radicals mentioned above under "$(C_3–C_5)$-cycloalkyl" and the cyclohexyl, cycloheptyl or cyclooctyl radical, and also bicyclic systems, such as, for example, the norbornyl group or the bicyclo[2,2,2]-octane radical;

the term "$(C_3–C_5)$-halocycloalkyl" is to be understood as meaning one of the abovementioned $(C_3–C_5)$-cycloalkyl radicals in which one or more, in the case of fluorine optionally also all, hydrogen atoms are replaced by halogen, preferably fluorine or chlorine, such as, for example, the 2,2-difluoro- or 2,2-dichlorocyclopropane group or the fluorocyclopentane radical;

the term "$(C_2–C_4)$-alkenyl" is to be understood as meaning, for example, the vinyl, allyl, 2-methyl-2-propenyl or 2-butenyl group;

the term "$(C_2–C_{20})$-alkenyl" is to be understood as meaning the abovementioned radicals and, for example, the 2-pentenyl, 2-decenyl or the 2-eicosenyl group;

the term "$(C_2–C_4)$-haloalkenyl" is to be understood as meaning a $(C_2–C_4)$-alkenyl group in which some of, or in the case of fluorine also all, the hydrogen atoms are replaced by halogen, preferably fluorine or chlorine;

the term "$(C_2–C_4)$-alkynyl" is to be understood as meaning, for example, the ethynyl, propargyl, 2-methyl-2-propynyl or 2-butynyl group;

the term ("$C_2–C_{20}$)-alkynyl" is to be understood as meaning the abovementioned radicals and, for example, the 2-pentynyl or the 2-decynyl group;

the term "$(C_2–C_4)$-haloalkynyl" is to be understood as meaning a $(C_2–C_4)$-alkynyl group in which some of, in the case of fluorine also all, the hydrogen atoms are replaced by halogen atoms, preferably fluorine or chlorine, or also the iodoethynyl group;

the term "dimethyl-$(C_1–C_8)$-alkyl-silyl-ethynyl" is to be understood as meaning, for example, the trimethylsilylethynyl or the tert-butyl-dimethyl-silyl-ethynyl group;

the term "$(C_1–C_4)$-hydroxyalkyl" is to be understood as meaning, for example, the hydroxymethyl, 1-hydroxyethyl, 2-hydroxyethyl, 1-hydroxy-1-methylethyl or the 1-hydroxypropyl group;

the term "$(C_1–C_4)$-alkanoyl" is to be understood as meaning, for example, the formyl, acetyl, propionyl, 2-methylpropionyl or butyryl group;

the term "$(C_1–C_{12})$-alkanoyl" is to be understood as meaning, for example, the abovementioned radicals and, for example, the valeroyl, pivaloyl, hexanoyl, decanoyl or the dodecanoyl group;

the term "$(C_2–C_4)$-haloalkanoyl" is to be understood as meaning a $(C_2–C_4)$-alkanoyl group in which some of, in the case of fluorine also all, the hydrogen atoms are replaced by halogen, preferably fluorine or chlorine;

the term "$(C_2–C_{12})$-haloalkanoyl" is to be understood as meaning a $(C_2–C_{20})$-alkanoyl group in which some of, in the case of fluorine also all, the hydrogen atoms are replaced by halogen atoms, preferably fluorine or chlorine;

the term "cyano-$(C_1–C_4)$-alkyl" is to be understood as meaning a cyanoalkyl group, the hydrocarbon radical of which has the meanings given under the term "$(C_1–C_4)$-alkyl";

the term "$(C_1–C_4)$-alkoxycarbonyl" is to be understood as meaning, for example, the methoxycarbonyl, ethoxycarbonyl, propoxycarbonyl, butoxycarbonyl or tert-butoxycarbonyl group;

the term "$(C_1–C_{12})$-alkoxycarbonyl" is to be understood as meaning the abovementioned radicals and, for example, the hexyloxycarbonyl, 2-methylhexyloxycarbonyl, decyloxycarbonyl or dodecyloxycarbonyl group;

the term "$(C_1–C_4)$-haloalkoxycarbonyl" is to be understood as meaning a $(C_1–C_4)$-alkoxycarbonyl group in which one or more, in the case of fluorine optionally also all, hydrogen atoms are replaced by halogen, preferably fluorine or chlorine;

the term "$(C_1–C_4)$-alkylthio" is to be understood as meaning an alkylthio group, the hydrocarbon radical of which has the meaning given under the term "$(C_1–C_4)$-alkyl";

the term "$(C_1–C_4)$-haloalkylthio" is to be understood as meaning a $(C_1–C_4)$-alkylthio group in which one or more, in the case of fluorine optionally also all, hydrogen atoms of the hydrocarbon part are replaced by halogen, in particular chlorine or fluorine; the term "$(C_1-C_4)$-alkylsulfinyl" is to be understood as meaning, for example, the methyl-, ethyl-, propyl-, isopropyl-, butyl-, isobutyl-, sec-butyl- or tert-butylsulfinyl group;

the term "$(C_1-C_4)$-alkylsulfonyl" is to be understood as meaning, for example, the methyl-, ethyl-, propyl-, isopropyl-, butyl-, isobutyl-, sec-butyl- or tert-butylsulfonyl group;

the terms "$(C_1-C_4)$-haloalkylsulfinyl" and "$(C_1-C_4)$-halo-alkylsulfonyl" are to be understood as meaning $(C_1-C_4)$-alkylsulfinyl and -sulfonyl radicals with the abovementioned meanings, in which one or more, in the case of fluorine optionally also all, hydrogen atoms of the hydrocarbon part are replaced by halogen, in particular chlorine or fluorine;

the term "$(C_1-C_4)$-alkoxy" is to be understood as meaning an alkoxy group, the hydrocarbon radical of which has the meaning given under the term "$(C_1-C_4)$-alkyl";

the term "$(C_1-C_4)$-haloalkoxy" is to be understood as meaning a haloalkoxy group, the halo-hydrocarbon radical of which has the meaning given under the term "$(C_1-C_4)$-haloalkyl";

the term "$(C_1-C_4)$-alkoxy-$(C_1-C_4)$-alkyl" is to be understood as meaning, for example, a 1-methoxyethyl group, a 2-methoxyethyl group, a 2-ethoxyethyl group, a methoxymethyl or ethoxymethyl group, a 3-methoxypropyl group or a 4-butoxybutyl group;

the terms "$(C_1-C_4)$-haloalkoxy-$(C_1-C_4)$-alkyl," "$(C_1-C_4)$-alkoxy-$(C_1-C_4)$-haloalkyl" and "$(C_1-C_4)$-haloalkoxy-$(C_1-C_4)$-haloalkyl" are to be understood as meaning $(C_1-C_4)$-alkoxy-$(C_1-C_4)$-alkyl radicals having the abovementioned meanings, in which one or more, in the case of fluorine optionally also all, hydrogen atoms of the corresponding hydrocarbon portions are replaced by halogen, preferably chlorine or fluorine;

the term "$(C_1-C_4)$-alkylthio-$(C_1-C_4)$-alkyl" is to be understood as meaning, for example, methylthiomethyl, ethylthiomethyl, propylthiomethyl, 2-methylthioethyl, 2-ethylthioethyl or 3-methylthiopropyl;

the term "aryl" is to be understood as meaning an isocyclic aromatic radical having preferably 6 to 14, in particular 6 to 12, carbon atoms, such as, for example, phenyl, naphthyl or biphenylyl, preferably phenyl;

the term "heterocyclyl" is to be understood as meaning a heteroaromatic or heteroaliphatic ring system, where "heteroaromatic ring system" is to be understood as meaning an aryl radical in which at least one CH group is replaced by N and/or at least two adjacent CH groups are replaced by S, NH or O, for example a radical of thiophene, furan, pyrrole, thiazole, oxazole, imidazole, isothiazole, isoxazole, pyrazole, 1,3,4-oxadiazole, 1,3,4-thiadiazole, 1,3,4-triazole, 1,2,4-oxadiazole, 1,2,4-thiadiazole, 1,2,4-triazole, 1,2,3-triazole, 1,2,3,4-tetrazole, benzo[b]thiophene, benzo[b]furan, indole, benzo[c]thiophene, benzo[c]furan, isoindole, benzoxazole, benzothiazole, benzimidazole, benzisoxazole, benzisothiazole, benzopyrazole, benzothiadiazole, benzotriazole, dibenzofuran, dibenzothiophene, carbazole, pyridine, pyrazine, pyrimidine, pyridazine, 1,3,5-triazine, 1,2,4-triazine, 1,2,4,5-tetrazine, quinoline, isoquinoline, quinoxaline, quinazoline, cinnoline, 1,8-naphthyridine, 1,5-naphthyridine, 1,6-naphthyridine, 1,7-naphthyridine, phthalazine, pyridopyrimidine, purine, pteridine or 4H-quinolizine;

and the term "heteroaliphatic ring system" is to be understood as meaning a $(C_3-C_8)$-cycloalkyl radical in which at least one carbon unit is replaced by O, S or a group $NR^{11}$, and $R^{11}$ is hydrogen, $(C_1-C_4)$-alkyl, $(C_1-C_4)$-alkoxy or aryl;

the term "arylthio" is to be understood as meaning, for example, the phenylthio or the 1- or 2-naphthylthio group;

the term "aryloxy" is to be understood as meaning, for example, the phenoxy or 1- or 2-naphthyloxy group;

the term "heterocyclyloxy" or "heterocylylthio" is to be understood as meaning one of the abovementioned heterocyclic radicals which are linked via an oxygen or sulfur atom;

the term "$(C_3-C_8)$-cycloalkoxy" or "$(C_3-C_8)$-cycloalkylthio" is to be understood as meaning one of the abovementioned $(C_3-C_8)$-cycloalkyl radicals which are linked via an oxygen or sulfur atom;

the term "aroyl" is to be understood as meaning, for example, the benzoyl, naphthoyl or the biphenylcarbonyl group;

the term "aryl-$(C_1-C_4)$-alkanoyl" is to be understood as meaning, for example, the phenylacetyl, 3-phenylpropionyl, 2-phenylpropionyl, 2-methyl-2-phenyl-propionyl, 4-phenylbutyryl or the naphthylacetyl group;

the term "$(C_3-C_8)$-cycloalkyl-$(C_1-C_4)$-alkanoyl" is to be understood as meaning, for example, the cyclopropylcarbonyl, cyclobutylcarbonyl, cyclopentylcarbonyl, cyclohexylcarbonyl, cyclohexylacetyl or the cyclohexylbutyryl group;

the term "heterocyclyl-$(C_1-C_4)$-alkanoyl" is to be understood as meaning, for example, the thenoyl, furoyl, nicotinoyl, thienylacetyl or the pyridine-propionyl group;

the term "$(C_3-C_8)$-cycloalkoxycarbonyl" is to be understood as meaning, for example, the cyclobutyloxycarbonyl, cyclopentyloxycarbonyl, cyclohexyloxycarbonyl or the cycloheptyloxycarbonyl group;

the term "$(C_3-C_8)$-cycloalkyl-$(C_1-C_4)$-alkoxycarbonyl" is to be understood as meaning, for example, the cyclopropylmethoxycarbonyl, cyclobutylmethoxycarbonyl, cyclopentyloxymethoxycarbonyl, cyclohexyloxymethoxycarbonyl, 1-(cyclohexyl)ethoxycarbonyl or the 2-(cyclohexyl)-ethoxycarbonyl group;

the term "aryl-$(C_1-C_4)$-alkoxycarbonyl" is to be understood as meaning, for example, the benzyloxycarbonyl, 1-naphthylmethoxycarbonyl, 2-naphthylmethoxycarbonyl, 1-phenyl-ethoxycarbonyl or the 2-phenyl-ethoxycarbonyl group;

the term "heterocyclyl-$(C_1-C_4)$-alkoxycarbonyl" is to be understood as meaning, for example, the thienylmethoxycarbonyl, furylmethoxycarbonyl, tetrahydrofurylmethoxycarbonyl or the pyridylethoxycarbonyl group;

the term "aryloxycarbonyl" is to be understood as meaning, for example, the phenoxycarbonyl, naphthoxycarbonyl or the biphenyloxycarbonyl group;

the term "heterocyclyloxycarbonyl" is to be understood as meaning, for example, the tetrahydropyran-4-oxycarbonyl group;

the term "$(C_1-C_{20})$-alkanoyloxy" is to be understood as meaning, for example, the formyloxy, acetoxy, propionyloxy, butyryloxy, pivaloyloxy, valeroyloxy or the hexanoyloxy group;

the term "$(C_2-C_{20})$-haloalkanoyloxy" is to be understood as meaning a $(C_2-C_{20})$-alkanoyloxy group in which one or more, in the case of fluorine optionally also all, hydrogen atoms of the hydrocarbon part are replaced by halogen, in particular fluorine or chlorine;

the term "$(C_3-C_8)$-cycloalkanoyloxy" is to be understood as meaning, for example, the cyclopropanoyloxy, cyclobutenoyloxy, cyclopentanoyloxy, cyclohexanoyloxy or the cycloheptanoyloxy group;

the term "$(C_3-C_8)$-cycloalkyl-$(C_1-C_4)$-alkanoyloxy" is to be understood as meaning, for example, the cyclopropylcarbonyloxy, cyclopropylacetoxy, cyclobutylcarbonyloxy, cyclopentylcarbonyloxy, cyclohexylcarbonyloxy, cyclohexylacetoxy or the 4-cyclohexyl-butyryloxy group;

the term "aroyloxy" is to be understood as meaning, for example, the benzoyloxy or the naphthoyloxy group;

the term "aryl-$(C_1-C_4)$-alkanoyloxy" is to be understood as meaning, for example, the benzoyloxy, naphthoyloxy, biphenylcarbonyloxy, phenylacetoxy or the phenylbutyryloxy group; the term "heterocyclyl-$(C_1-C_4)$-alkanoyloxy" is to be understood as meaning, for example, the thienylcarbonyloxy, thienylacetoxy, pyridylcarbonyloxy or the pyrimidinylcarbonyloxy group;

the term "$(C_1-C_{20})$-alkylsulfonyloxy" is to be understood as meaning, for example, the methane-, ethane-, butane- or hexanesulfonyloxy group;

the term "arylsulfonyloxy" is to be understood as meaning, for example, the phenylsulfonyloxy or the toluenesulfonyloxy group.

The substituents with which the various aliphatic, aromatic and heterocyclic ring systems can be provided include, for example, halogen, nitro, cyano, di-$(C_1-C_4)$-alkylamino, $(C_1-C_4)$-alkyl, $(C_3-C_8)$-cycloalkyl, $(C_1-C_4)$-alkanoyl, $(C_1-C_4)$-alkoxycarbonyl, $(C_1-C_4)$-trialkylsilyl, $(C_1-C_4)$-alkoxy, $(C_1-C_4)$-alkoxy-$(C_1-C_4)$-alkyl, $(C_1-C_2)$-alkoxy-$[CH_2CH_2O]_{1,2}$-ethoxy, $(C_1-C_4)$-alkylthio, $(C_1-C_4)$-alkylsulfinyl, $(C_1-C_4)$-alkylsulfonyl, phenyl, benzyl, phenoxy, halophenoxy, $(C_1-C_4)$-alkylphenoxy, $(C_1-C_4)$-alkoxyphenoxy, phenylthio, heterocyclyl, heterocyclylthio, heterocyclyloxy, haloheterocyclyloxy, alkylheterocyclyloxy or alkoxyheterocyclyloxy, where, in the alkyl radicals and the radicals derived therefrom, one or more hydrogen atoms, in the case of fluorine also up to the maximum number, can be replaced by halogen, preferably chlorine or fluorine, and where, in the case where these substituernts are $(C_1-C_4)$-alkyl, these can also be linked cyclically and one or two aliphatic carbon units in these fused ring systems, such as, for example, an indane, di-, tetra- or decahydronaphthyl or benzocycloheptane system, can be replaced by heteroatom units, such as oxygen or sulfur, and one or more hydrogen atoms, in the case of fluorine also up to the maximum number, on the aliphatic carbon atom units can be replaced by halogen or $(C_1-C_4)$-alkyl.

Furthermore, the definition that "in the alkyl, alkenyl or alkynyl radicals mentioned, one or more, preferably up to three, non-adjacent saturated carbon units can be replaced by a carbonyl group or by heteroatom units, such as oxygen, $S(O)_x$, where x=0, 1 or 2, $NR^6$ or $SiR^7R^8$, in which $R^6$ is hydrogen, $(C_1-C_4)$-alkyl, $(C_1-C_4)$-alkoxy or $(C_1-C_4)$-alkanoyl and $R^7$ and $R^8$ are $(C_1-C_4)$-alkyl, preferably methyl, and wherein, furthermore, 3 to 12 atoms of these hydrocarbon radicals optionally modified as above can form a ring, and these hydrocarbon radicals, with or without the variations mentioned, can optionally be substituted by one or more, preferably up to three, in the case of fluorine up to the maximum number of, identical or different radicals from the series consisting of halogen, aryl, aryloxy, arylthio, cycloalkoxy, cycloalkylthio, heterocyclyl, heterocyclyloxy, heterocyclylthio, alkanoyl, cycloalkanoyl, haloalkanoyl, aroyl, arylalkanoyl, cycloalkylalkanoyl, heterocyclylalkanoyl, alkoxycarbonyl, haloalkoxycarbonyl, cycloalkoxycarbonyl, cycloalkylalkoxycarbonyl, arylalkoxycarbonyl, heterocyclylalkoxycarbonyl, aryloxycarbonyl, heterocyclyloxycarbonyl, alkanoyloxy, haloalkanoyloxy, cycloalkanoyloxy, cycloalkylalkanoyloxy, aroyloxy, arylalkanoyloxy, heterocycloalkanoyloxy, alkylsulfonyloxy, arylsulfonyloxy, hydroxyl, cyano, thiocyano and nitro, where the cycloaliphatic, aromatic or heterocyclic ring systems among the substituents just mentioned can be unsubstituted or provided with up to three, in the case of fluorine also up to the maximum number of, identical or different substituents", is to be understood as meaning, for example:

alkoxyalkyl radicals, such as, for example, the methoxymethyl, methoxyethyl or ethoxyethyl group; or alkoxy-alkoxy-alkyl radicals, such as, for example, the methoxy- or the ethoxy-ethoxy ethyl group; or alkylthioalkyl radicals, such as, for example, the methyl- or the ethylthioethyl group; or alkylsulfinyl-alkyl radicals, such as, for example, the methyl- or ethylsulfinylethyl group; or alkylsulfonyl-alkyl radicals, such as, for example, the methyl- or ethylsulfonylethyl group; or alkyl-dialkylsilyl-alkyl, preferably alkyl-dimethylsilyl-alkyl radicals, such as, for example, the trimethylsilylmethyl or the trimethylsilylethyl group; or trialkylsilyl, preferably alkyldimethylsilyl radicals, such as, for example, the trimethylsilyl, ethyldimethylsilyl, tertbutyldimethylsilyl or the octyldimethylsilyl group; or cycloalkyldialkylsilyl, preferably cycloalkyldimethylsilyl radicals, such as, for example, the cyclohexyldimethylsilyl group; or aryldialkylsilyl, preferably aryldimethylsilyl radicals, such as, for example, the phenyldimethylsilyl group; or arylalkyldialkylsilyl, preferably arylalkyldimethylsilyl radicals, such as, for example, the benzyldimethylsilyl or the phenylethyldimethylsilyl group; or alkanoylalkyl radicals, such as, for example, the acetylmethyl or the pivaloylmethyl group; or cycloalkanoylalkyl radicals, such as, for example, the cyclopropylcarbonylmethyl or the cyclohexylcarbonylmethyl group; or haloalkanoylalkyl radicals, such as, for example, the trifluoro- or trichloroacetylmethyl group; or aroylalkyl radicals, such as, for example, the benzoyl or naphthoylalkyl radicals; or arylakanoylalkyl radicals, such as, for example, the phenylacetylmethyl group; or heterocyclylcarbonylalkyl radicals, such as, for example, the thienyl- or pyridylacetylmethyl group; or aryl-alkyl radicals, such as, for example, the benzyl, the 2-phenylethyl, the 1-phenylethyl or the 1-methyl-1-phenylethyl group, the 3-phenylpropyl or the 4-phenylbutyl group, the 2-methyl-2-phenyl-ethyl group or the 1-methyl- or 2-methyl-naphthyl group; or heterocyclylalkyl radicals, such as, for example, the thienylmethyl, pyridylmethyl, furfuryl, tetrahydrofurfuryl, tetrahydropyranylmethyl or the 1,3-dioxolane-2-methyl group; or aryloxyalkyl radicals, such as, for example, the phenoxymethyl or naphthoxymethyl group; or cycloalkyl radicals, which are monocyclic, such as, for example, the cyclopropyl, cyclobutyl, cyclopentyl, cyclohexyl, cycloheptyl or cyclooctyl radical, bicyclic, such as, for example, the norbornyl radical or the bicyclo[2.2.2]octane radical, or fused, such as the decahydronaphthyl radical;

alkyl-cycloalkyl radicals, such as, for example, the 4-methyl- or the 4-tert-butylcyclohexyl group or the 1-methyl-cyclopropyl, -cyclobutyl, -cyclopentyl or -cyclohexyl group;

cycloalkyl-alkyl radicals, such as, for example, the cyclohexylmethyl or -ethyl group;

or also haloalkyl derivatives of the corresponding groups, such as, for example, haloalkyl, haloalkoxyalkyl, alkoxy-haloalkyl, haloalkyl-cycloalkyl or halocycloalkyl radicals.

The explanation given above applies accordingly to homologs and radicals derived therefrom.

The present invention relates to the compounds of the formula I in the form of the free base or an acid addition salt. Acids which can be used for salt formation are inorganic acids, such as hydrochloric acid, hydrobromic acid, nitric acid, sulfuric acid or phosphoric acid, or organic acids, such as formic acid, acetic acid, propionic acid, malonic acid, oxalic acid, fumaric acid, adipic acid, stearic acid, oleic acid, methanesulfonic acid, benzenesulfonic acid or toluenesulfonic acid.

In addition to the cis/trans isomerism mentioned for the hetero-aliphatic system including the groups Y and Z, the compounds of the formula I in some cases contain one or more asymmetric carbon atoms or stereoisomers on double bonds. Enantiomers or diastereomers can therefore occur. The invention relates both to pure isomers and to mixtures thereof. The mixtures of diastereomers can be separated into the components by customary methods, for example by selective crystallization from suitable solvents or by chromatography. Racemates can be separated into the enantiomers by customary methods, thus, for example, by salt formation with an optically active acid, separation of the diastereomeric salts and liberation of the pure enantiomers by means of a base.

The invention furthermore relates to a process for the preparation of compounds of the formula I which comprises reacting a compound of the formula II

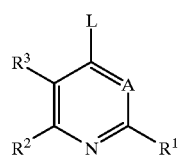

(II)

in which A, R$^1$, R$^2$ and R$^3$ have the meanings given under formula I and L is a leaving group, for example halogen, alkylthio, alkanesulfonyloxy or arylsulfonyloxy, alkylsulfonyl or arylsulfonyl, with a nucleophile of the formula III

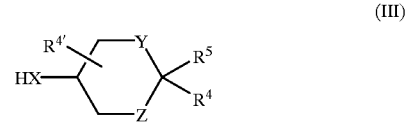

(III)

in which X, Y, Z, R$^4$, R$^{4'}$ and R$^5$ have the meanings given above under formula I, and, in the compounds of the formula I obtained in this manner or in another manner, optionally further derivatizing the nitrogen-containing heterocyclic radical or the side chain R$^5$.

The substitution reaction described above is known in principle. The leaving group Z can be varied within wide limits and can be, for example, a halogen atom, such as fluorine, chlorine, bromine or iodine, or alkylthio, such as methyl- or ethylthio, or alkanesulfonyloxy, such as methane-, trifluoromethane- or ethanesulfonyloxy, or arylsulfonyloxy, such as benzenesulfonyloxy or toluenesulfonyloxy, or alkylsulfonyl, such as methyl- or ethylsulfonyl, or arylsulfonyl, such as phenyl- or toluenesulfonyl.

The above-mentioned reaction is carried out in a temperature range from 20 to 150° C., expediently in the presence of a base and if appropriate in an inert organic solvent, such as N,N-dimethylformamide, N,N-dimethylacetamide, dimethyl sulfoxide, N-methylpyrrolidin-2-one, dioxane, tetrahydrofuran, 4-methyl-2-pentanone, methanol, ethanol, butanol, ethylene glycol, ethylene glycol dimethyl ether, toluene, chlorobenzene or xylene. Mixtures of the solvents mentioned can also be used.

Suitable bases in the case were X is oxygen are, for example, alkali metal or alkaline earth metal carbonates, bicarbonates, amides or hydrides, such as sodium carbonate, sodium bicarbonate, potassium carbonate, sodium amide or sodium hydride, and in the case where X is NH, these are, for example, alkali metal or alkaline earth metal carbonates, bicarbonates, hydroxides, amides or hydrides, such as sodium carbonate, sodium bicarbonate, potassium carbonate, sodium hydroxide, sodium amide or sodium hydride, or organic bases, such as triethylamine or pyridine. A second equivalent of an amine of the formula III can also be employed as an auxiliary base.

The compounds of the formula II required as starting substances are in most cases known from the literature or can be prepared by methods analogous to those known from the literature (cf. EP 370 391, EP 470 600, DOS 43 31 179, DOS 44 04 702, incorporated herein by reference).

To prepare the nucleophiles of the formula III, suitably substituted 1,3-dioxan-5-ones or 1,3-dithian-5-ones are used as starting substances (A. A. Marei, R. A. Raphael, J. Chem. Soc. 1960, 886; H. Vorbrüggen, Acta Chem. Scand., 1982, 420; D. Enders, B. Bockstiegel, Synthesis 1989, 493; A. Luttringhaus, M. Mohr, N. Engelhard, Liebigs Ann. Chem. 661 (1963) 84; Y. M. Kobayashi, J. Lambrecht, J. C. Jochims, U. Burkert, Chem. Ber. 111, 3442 (1978), incorporated herein by reference) and these are converted into the corresponding amines by reductive amination (H$_2$, NH$_3$, metal catalyst or ammonium acetate/sodium cyanoborohydride) or Leuckart-Wallach reduction, or into the corresponding alcohols by reduction with a complex metal hydride. To prepare the particularly preferred cis derivatives, a rhodium or a rhodium/palladium mixed catalyst is particularly suitable for the reductive amination, and particularly suitable complex metal hydrides are those which carry alkyl substituents of large bulk, in addition to the hydrogen, such as, for example, ®L-Selectride.

Alternatively, there is the possibility of converting the 1,3-dioxan-5-ones into the corresponding alcohols by reduction with a complex metal hydride ($LiAlH_4$, $NaBH_4$), and obtaining the amines ($H_2$/Pd or $LiAlH_4$) from these via the mesylate or tosylate ($CH_3SO_2Cl$/$CH_3C_6H_4SO_2Cl$, pyridine) and azide ($NaN_3$, dimethylformamide) (cf. D. Lednicer, D. E. Emmert, R. Lahti, A. D. Rudzik, J. Med. Chem. 15, 1239, (1972), incorporated herein by reference). The alcohols mentioned can also be obtained directly from aldehyde and glycerol under acid catalysis (P. E. Verkade, J. D. van Roon, Rec. Trav. Chim. Pays Bas, 61, 831 (1942); E. Juaristi, S. Antunez, Tetrahedron 48, 5941 (1992), incorporated herein by reference). The invention furthermore relates to a process for the preparation of compounds of the formula I, which comprises reacting a compound of the formula IV

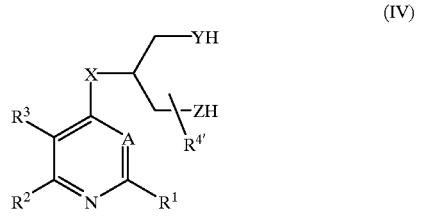

(IV)

in which $R^1$, $R^2$, $R^3$, $R^{4'}$, A, X, Y and Z have the meanings given above for formula I, with a compound of the formula V or V'

(V)

(V')

in which $R^4$ and $R^5$ have the meanings given above for formula I and $R^6$ are the same or different and are ($C_1$–$C_8$)-alkyl, preferably ($C_1$–$C_4$)-alkyl, and, in the compounds of the formula I obtained in this manner or in another manner, further varying the nitrogen-containing heterocyclic radical or the side chain $R^5$.

The reaction is expediently carried out by allowing the compounds of the formula IV and of the formula V to react in the presence of an acid catalyst in a temperature range of 20–200° C., preferably between 60° and 150° C., in bulk or in an inert organic solvent.

The ketalization reaction described above is known in principle. It is carried out in a temperature range of 20–200° C., preferably between 60° and 150° C., in the presence of an acid dehydrating catalyst, in bulk or in an inert solvent. Suitable catalysts are, for example, hydrochloric acid, sulfuric acid, phosphoric acid, sodium hydrogen sulfate, sulfonic acids, such as methane- or toluenesulfonic acid, phosphorus-V oxide, iron(III) chloride, zinc chloride, anhydrous copper sulfate, iodine or also acid ion exchangers, such as, for example, ®Amberlite IR-120. The water formed during the reaction is expediently removed from the reaction mixture by distillation, if appropriate under reduced pressure, or by azeotropic distillation using an entraining agent. Suitable entraining agents are, for example, benzene, toluene, xylene or petroleum ether.

The reaction of the compounds of the formula IV with the compounds of the formula V' is carried out in analogy to the reaction of the compounds of the formula IV with the compounds of the formula V, in bulk or in an inert organic solvent, such as benzene, toluene, xylene or petroleum ether. The compounds of the formula $V^1$ are used in an equimolar ration or in excess. The alcohol formed during the reaction is expediently removed by distillation from the reaction mixture.

The compounds of the formula IV required as starting substances can be synthesized as follows:

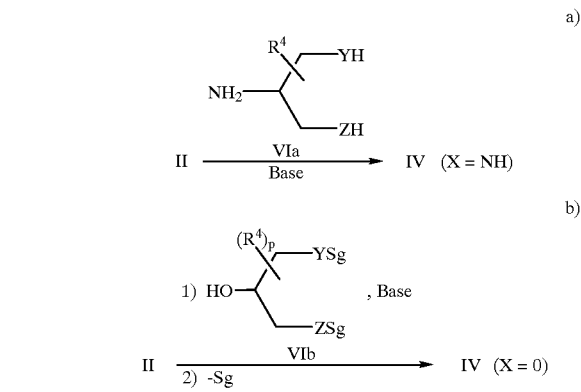

The reaction conditions for the reactions described under a) and b) correspond to those for the preparation of the compounds III from the compounds of the formula II. The educts of the formula VIa are commercially obtainable, are known from the literature or can be synthesized by processes analogous to known processes (cf. M. Kujima, Yakugaku Zasshi 90, (1970), 670, incorporated herein by reference).

Compounds of the formula VIb are employed in a protected form. A suitable protective group is, for example, the benzyl group, which is removed by hydrogenolysis after the reaction has taken place. The starting materials of the formula VIb are commercially obtainable, are known from the literature or can be synthesized by processes analogous to known processes.

The active compounds have a good plant tolerance and favourable toxicity with respect to warm-blooded animals and are suitable for controlling animal pests, in particular insects, arachnids, helminths and mollusks, especially preferably for controlling insects and arachnids which are encountered in agriculture, in animal husbandry, in forestry, in the preservation of stored products and materials and in the hygiene sector. They are active against normally sensitive and resistant species and all or individual stages of development. The abovementioned pests include:

From the order of the Acarina, for example, *Acarus siro*, Argas spp., Ornithodoros spp., *Dermanyssus gallinae, Eriophyes ribis, Phyllocoptruta oleivora*, Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa*, Panonychus spp., tetranychus spp., Eotetranychus spp., oligonychus spp. and Eutetranychus spp.

From the order of the Isopoda, for example, *Oniscus asselus, Armadium vulgar* and *Porcellio scaber.*

From the order of the Diplopoda, for example, *Blaniulus guttulatus.*

From the order of the Chilopoda, for example, *Geophilus carpophagus* and Scutigera spp.

From the order of the Symphyla, for example, *Scutigerella immaculata*.

From the order of the Thysanura, for example, *Lepisma saccharina*.

From the order of the Collembola, for example, *Onychiurus armatus*.

From the order of the Orthoptera, for example, *Blatta orientalis, Periplaneta americana, Leucophaea madeirae, Blatella germanica, Acheta domesticus*, Gryllotalpa spp., *Locusta migratoria migratorioides, Melanoplus differentialis and Schistocerca gregaria*.

From the order of the Isoptera, for example, Reticulitermes spp.

From the order of the Anoplura, for example, *Phylloera vastatrix*, Pemphigus spp., *Pediculus humanus corporis*, Haematopinus spp. and Linognathus spp.

From the order of the Mallophaga, for example, Trichodectes pp. and Damalinea spp.

From the order of the Thysanoptera, for example, *Hercinothrips femoralis, Thrips tabaci* and Frankliniella spp.

From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum*, Aphis spp., *Brevicoryne brassicae, Cryptomyzus ribis, Doralis fabae, Doralis pomi, Eriosoma lanigerum, Hyalopterus arundinis, Macrosiphum avenae*, Myzus spp., *Phorodon humuli*, Rhopalosiphum padi, Empoasca spp., *Euscelus bilobatus, Nephotettix cincticeps, Lecanium corni, Saissetia oleae, Laodelphax striatellus, Nilaparvata lugens, Aonidiella aurantii, Aspidiotus hederae*, Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea*, Lymantria spp., *Bucculatrix thurberiella, Phyllocnistis citrella*, Agrotis spp., Euxoa spp., Feltia spp., *Earias insulana*, Heliothis spp., *Laphygma exigua, Mamestra brassicae, Panolis flammea, Prodenia litura*, Spodoptera spp., *Trichoplusia ni, Carpocapsa pomonella*, Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima, Tortrix viridana*, Cuaphalocrocis spp. and Manduca spp.

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae*, Diabrotica spp., *Psylloides chrysocephala, Epilachna varivestis*, Atomaria spp., *Oryzaephilus surinamensis*, Anthonumus spp., Sitophilus spp., *Otiorrhynchus sulcatus, Cosmopolites sordidus, Ceuthorrynchus assimilis, Hypera postica*, Dermestes spp., Trogoderma, Anthrenus spp., Attagenus spp., Lyctus spp., *Meligethes aeneus*, Ptinus spp., *Niptus hololeucus, Gibbium psylloides*, Tribolium spp., *Tenebrio molitor*, Agriotes spp., Conoderus spp., *Melolontha melolontha, Amphimallon solstitialis, Costelytra zealandica* and Lissorhoptus spp.

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster*, Musca spp., Fannia spp., *Calliphora erythrocephala*, Lucilia spp., Chrysomyia spp., Cuterebra spp., Gastrophilus spp., Hypobosca spp., Stomoxys spp., Oestrus spp., Hypoderma spp., Tabanus spp., Tannia spp., *Bibio hortulanus, Oscinella frit*, Phorbia spp., *Pegomyia hyoscyami, Ceratitis capitata, Dacus oleae* and *Tipula paludosa*.

From the order of the Siphonaptera, for example, *Xenopsylla cheopsis* and Ceratophyllus spp.

From the order of the Arachnida, for example, *Scorpio maurus* and *Latrodectus mactans*.

From the class of helminths, for example, Haemonchus, Trichostrongulus, Ostertagia, Cooperia, Chabertia, Strongyloides, Oesophagostomum, Hyostronguluse Ancylostoma, Ascaris and Heterakis, as well as Fasciola.

From the class of Gastropoda, for example, Deroceras spp., Anion spp., Lyinnaea spp., Galba spp., Succinea spp., Biomphalaria spp., Bulinus spp. and oncomelania spp. From the class of Bivalva, for example, Dreissena spp.

The phytoparasitic nematodes which can be controlled according to the invention include, for example, the root-parasitic soil nematodes, such as, for example, those of the genera Meloidogyne (root gall nematodes, such as *Meloidogyne incognita, Meloidogyne hapla* and *Meloidogyne javanica*), Heterodera and Globodera (cyst-forming nematodes, such as *Globodera rostochiensis, Globodera pallida* and *Heterodera trifohli*) and of the genera Radopholus (such as *Radopholus similis*), Pratylenchus (such as *Pratylenchus neglectus, Pratylenchus penetrans* and *Pratylenchus curvitatus*), Tylenchulus (such as *Tylenchulus semipenetrans*), Tylenchorhynchus (such as *Tylenchorhynchus dubius* and *Tylenchorhynchus claytoni*), Rotylenchus (such as *Rotylencus robustus*), Heliocotylenchus (such as *Heliocotylenchus multicinctus*), Belonoaimus (such as *Belonoaimus longicaudatus*), Longidorus (such as *Longidorus elongatus*), Trichodorus (such as *Trichodorus primitivus*) and Xiphinema (such as *Xiphinema index*).

The nematode genera Ditylenchus (stem parasites, such as *Ditylenchus dipsaci* and *Ditylenchus destructor*), Aphelenchoides (leaf nematodes, such as *Aphelenchoides ritzemabosi*) and Anguina (blossom nematodes, such as *Anguina tritici*) can furthermore be controlled with the compounds according to the invention.

The invention also relates to compositions, in particular insecticidal and acaricidal compositions, which comprise the compounds of the formula I in addition to suitable formulation auxiliaries.

The compositions according to the invention in general comprise the active compounds of the formula I to the extent of 1 to 95% by weight.

They can be formulated in various ways, depending on how this is determined by the biological and/or chemicophysical parameters. Suitable formulation possibilities are therefore:

Wettable powders (WP), emulsifiable concentrates (EC), aqueous solutions (SL), emulsions, sprayable solutions, oil- or water-based dispersions, suspension concentrates (SC), suspoemulsions (SE), dusting powders (DP), seed dressings, granules in the form of microgranules, sprayed granules, absorption granules and adsorption granules, water-dispersible granules (WG), ULV formulations, microcapsules, waxes or baits. These individual types of formulation are known in principle and are described, for example, in: Winnacker-Küchler, "Chemische Technologie" [Chemical Technology], Volume 7, C. Hauser Verlag Munich, 4th Edition 1986; van Falkenberg, "Pesticides Formulations", Marcel Dekker N.Y., 2nd Edition 1972–73; K. Martens, "Spray Drying Handbook", 3rd Edition 1979, G. Goodwin Ltd. London, incorporated herein by reference.

The necessary formulation auxiliaries, such as inert materials, surfactants, solvents and further additives, are likewise known and are described, for example, in: Watkins, "Handbook of Insecticide Dust Diluents and Carriers", 2nd Edition, Darland Books, Caldwell N.J.; H. v. Olphen, "Introduction to Clay Colloid Chemistry", 2nd Edition, J. Wiley & Sons, N.Y.; Marsden, "Solvents Guide", 2nd Edition, Interscience, N.Y. 1950; McCutcheon's, "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active ethylene oxide adducts], Wiss. Verlagsgesell., Stuttgart 1967; Winnacker-Küchler, "Chemische Technologiel" [Chemical Technology], Volume 7, C. Hauser Verlag Munich, 4th Edition 1986, incorporated herein by reference.

Combinations with other substances having a pesticidal action, fertilizers and/or growth regulators can be prepared on the basis of these formulations, for example in the form of a ready-to-use formulation or as a tank mix. Wettable powders are preparations which are uniformly dispersible in water and which, alongside the active compound, and in addition to a diluent or inert substance, also comprise wetting agents, for example poly-oxyethylated alkylphenols, polyoxyethylated fatty alcohols or alkyl- or alkylphenol-sulfonates, and dispersing agents, for example sodium lign-insulfonate or sodium 2,2'-dinaphthylmethane-6,6'-disulfonate. Emulsifiable concentrates are prepared by dissolving the active compound in an organic solvent, for example butanol, cyclohexanone, dimethylformamide, xylene or also higher-boiling aromatics or hydrocarbons, with the addition of one or more emulsifiers. Emulsifiers which can be used are, for example: calcium alkylarylsulfonates, such as Cadodecylbenzenesulfonate, or nonionic emulsifiers, such as fatty acid polyglycol esters, alkylaryl polyglycol ethers, fatty alcohol polyglycol ethers, propylene oxide/ethylene oxide condensation products, alkyl polyethers, sorbitan fatty acid esters, polyoxyethylene sorbitan fatty acid esters or polyoxyethylene sorbitol esters.

Dusting powders are obtained by grinding the active compound with finely divided solid substances, for example talc, naturally occurring clays, such as kaolin, bentonite and pyrophillite, or diatomaceous earth. Granules can be prepared either by spraying the active compound onto granular inert material capable of adsorption or by applying active compound concentrates to the surface of carrier substances, such as sand, kaolinites or granular inert material, by means of adhesives, for example polyvinyl alcohol, sodium polyacrylate or mineral oils. Suitable active compounds can also be granulated in the manner customary for the preparation of fertilizer granules—if desired as a mixture with fertilizers.

In wettable powders, the active compound concentration is, for example, about 10 to 90% by weight, the remainder to make up 100% by weight comprising customary formulation constituents. In emulsifiable concentrates, the active compound concentration can be about 5 to 80% by weight. Dust-like formulations usually comprise 5 to 20% by weight of active compound, and sprayable solutions about 2 to 20% by weight. In granules, the content of active compound partly depends on whether the active compound is present in liquid or solid form and what granulating auxiliaries, fillers and the like are used.

In addition, the active compound formulations mentioned comprise, if appropriate, the particular customary tackifiers, wetting agents, dispersing agents, emulsifiers, penetration agents, solvents, fillers or carriers.

For use, the concentrates in the commercially available form are diluted in the customary manner, if appropriate, for example by means of water in the case of wettable powders, emulsifiable concentrates, dispersions and in some cases also microgranules. Dust-like and granular formulations as well as sprayable solutions are usually not diluted further with additional inert substances before use.

The required amount applied varies with external conditions, such as temperature, humidity and the like. It can vary within wide limits, for example between 0.0005 and 10.0 kg/ha or more of active substance, but is preferably between 0.001 and 5 kg/ha.

The active compounds according to the invention can be present in their commercially available formulations and in the use forms prepared from these formulations as mixtures with other active compounds, such as insecticides, attractants, sterilizing agents, acaricides, nematicides, fungicides, growth-regulating substances or herbicides.

The pest control agents include, for example, phosphoric acid esters, carbamates, carboxylic acid esters, formamidines, tin compounds, substances produced by microorganisms and the like. Preferred partners for the mixtures are 1. from the group of phosphorus compounds acephate, azamethiphos, azinphos-ethyl-, azinphosmethyl, bromophos, bromophos-ethyl, chlorfenvinphos, chlormephos, chlorpyrifos, chlorpyrifos-methyl, demeton, demeton-S-methyl, demeton-S-methyl sulfone, dialifos, diazinon, dichlorvos, dicrotophos, O,O-1,2,2,2-tetrachloroethyl phosphorthioate (SD 208 304), dimethoate, disulfoton, EPN, ethion, ethoprophos, etrimfos, famphur, fenamiphos, fenitriothion, fensulfothion, fenthion, fonofos, formothion, heptenophos, isozophos, isothioate, isoxathion, malathion, methacrifos, methamidophos, methidathion, salithion, mevinphos, monocrotophos, naled, omethoate, oxydemeton-methyl, parathion, parathion-methyl, phenthoate, phorate, phosalone, phosfolan, phosmet, phosphamidon, phoxim, pirimiphos, primiphos-ethyl, pirimiphos-methyl, profenofos, propaphos, proetamphos, prothiofos, pyraclofos, pyridapenthion, quinalphos, sulprofos, temephos, terbufos, tetrachlorvinphos, thiometon, triazophos, trichlorphon, vamidothion;

2. from the group of carbamates aldicarb, 2-secbutylphenyl methylcarbamate (BPMC), carbaryl, carbofuran, carbosulfan, cloethocarb, benfuracarb, ethiofencarb, furathiocarb, isoprocarb, methomyl, 5-methyl-m-cumenyl butyryl(methyl)carbamate, oxamyl, pirimicarb, propoxur, thiodicarb, thiofanox, ethyl 4,6,9-triaza-4-benzyl-6,10-dimethyl-8-oxa-7-oxo-5,11-dithia-9-dodecenoate (OK 135), 1-methylthio(ethylideneamino) N-methyl-N-(morpholinothio)carbamate (UC 51717);

3. from the group of carboxylic acid esters allethrin, alphametrin, 5-benzyl-3-furylmethyl (E)-(1R)-cis, 2,2-dimethyl-3-(2-oxothiolan-3-ylidenemethyl)cyclopropanecarboxylate, bioallethrin, bioallethrin ((S)-cyclopentyl isomer), bioresmethrin, biphenate, (RS)-1-cyano-1-(6-phenoxy-2-pyridyl)methyl (1RS)-trans-3-(4-tert-butylphenyl)-2,2-dimethylcyclopropanecarboxylate (NCI 85193), cycloprothrin, cyhalothrin, cythithrin, cypermethrin, cyphenothrin, deltamethrin, empenthrin, esfenvalerate, fenfluthrin, fenpropathrin, fenvalerate, flucythrinate, flumethrin, fluvalinate (D isomer), permethrin, pheothrin ((R) isomer), d-pralethrin, pyrethrins (naturally occurring products), resmethrin, tefluthrin, tetramethrin and tralomethrin;
4. from the group of amidines amitraz, chlordimeform;
5. from the group of tin compounds cyhexatin, fenbutatin oxide;
6. others abamectin, Bacillus thuringiensis, bensultap, binapacryl, bromopropylate, buprofezin, camphechlor, cartap, chlorobenzilate, chlorfluazuron, 2-(4-chlorophenyl)-4,5-di-phenylthiophene (UBI-T 930), chlorfentezine, 2-naphthylmethyl cyclopropanecarboxylate (Ro 12-0470), cyromazin, N-(3,5-dichloro-4-(1,1,2,3,3,3-hexafluoro-1-propyloxy)phenyl)carbamoyl)-2-chlorobenzocarboximide acid ethyl ester, DDT, dicofol, N-(N-(3,5-di-chloro-4-(1,1,2,2-tetrafluoroethoxy)phenylamino)carbonyl)-2,6-difluorobenzamide (XRD 473), diflubenzuron, N-(2,3-dihydro-3-methyl-1,3-thiazol-2-ylidene)-2,4-xylidene, dinobuton, dinocap, endosulfan, ethofenprox, (4-ethoxyphenyl)(dimethyl)(3-(3-phenoxyphenyl)propyl)silane, (4-ethoxyphenyl)(3-(4-fluoro-3-phenoxyphenyl)propyl)dimethylsilane, fenoxycarb, 2-fluoro-5-( 4-(4-ethoxyphenyl)-4-methyl-1-pentyl)diphenyl ether (MTI 800), granulosis and nuclear polyhedrosis viruses, fenthiocarb, flubenzimine, flucycloxuron, flufenoxuron, gamma-HCH, hexythiazox, hydramethylnon (AC 217300), ivermectin, 2-nitromethyl-4,5-dihydro-6H-thiazine (DS 52618), 2-nitromethyl-3,4-dihydrothiazole (SD 35651), 2-nitromethylene-1,2-thiazinan-3-ylcarbamaldehyde (WL 108477), propargite, teflubenzuron, tetradifon, tetrasul, thiocyclam, trifumuron, imidacloprid.

The active compound content of the use forms prepared from the commercially available formulations can be from 0.00000001 to 95% by weight of active compound, preferably between 0.00001 and 1% by weight.

The active compounds are used in a customary manner appropriate for the use forms.

The active compounds according to the invention are also suitable for controlling endo- and ectoparasites in the veterinary medicine field and in the field of animal husbandry.

The active compounds according to the invention are used here in a known manner, such as by oral use in the form of, for example, tablets, capsules, potions or granules, by means of dermal use in the form of, for example, dipping, spraying, pouring-on, spotting-on and dusting, and by parenteral use in the form of, for example, injection.

The novel compounds of the formula I according to the invention can accordingly also particularly advantageously be used in livestock husbandry (for example cattle, sheep, pigs and poultry, such as chickens, geese and the like). In a preferred embodiment of the invention, the novel compounds are administered orally to the animals, if appropriate in suitable formulations (cf. above) and if appropriate with the drinking water or feed. Since excretion in the faeces takes place in an active manner, the development of insects in the faeces of the animals can be prevented very easily in this way. The dosages and formulations suitable in each case depend in particular on the species and the development stage of the stock animals and also on the pressure of infestation, and can easily be determined and specified by the customary methods. The novel compounds can be employed in cattle, for example, in dosages of 0.01 to 1 mg/kg of body weight.

The compounds of the formula I according to the invention are also distinguished by an outstanding fungicidal action. Fungal pathogens which have already penetrated into the plant tissue can successfully be controlled curatively. This is particularly important and advantageous for those fungal diseases which can no longer be controlled effectively with the otherwise customary fungicides after infection has occurred. The action spectrum of the compounds claimed includes various economically important phytopathogenic fungi, such as, for example, Plasmopara viticola, Phytophthora infestans, Erysiphe graminis, Pyricularia oryzae, Pyrenophora teres, Leptosphaeria nodorum and Pellicularia sasakii and Puccinia recondita.

In addition, the compounds according to the invention are also suitable for use in industrial fields, for example as wood preservatives, as preservatives in paints and in cooling lubricants for metalworking, or as preservatives in drilling and cutting oils.

The active compounds according to the invention can be used in their commercially available formulations either by th emselves or in combination with other fungicides known from the literature.

The following products, for example, may be mentioned as fungicides which are known from the literature and can be combined according to the invention with the compounds of the formula I: aldimorph, andoprim, anilazine, BAS 480F, BAS 450F, BAS 490F, benalaxyl, benodanil, benomyl, binapacryl, bitertanol, bromuconazole, buthiobate, captafol, captan, carbendazim, carboxin, CGA 173506, cyprodinil, cyprofuram, dichlofluanid, dichlomezin, diclobutrazol, diethofencarb, difenconazol (CGA 169374), difluconazole, dimethirimol, dimethomorph, diniconazole, dinocap, dithianon, dodemorph, dodine, edifenfos, ethirimol, etridiazol, epoxiconazole, fenbuconazole, fenarimol, fenfuram, fenpiclonil, fenpropidin, fenpropimorph, fentin acetate, fentin hydroxide, ferimzone (TF 164), fluazinam, fluobenzimine, fludioxinil, fluquinconazole, fluorimide, flusilazole, flutolanil, flutriafol, folpet, fosetylaluminium, fuberidazole, fulsulfamide (MT-F 651), furalaxyl, furconazole, furmecyclox, guazatine, hexaconazole, ICI A5504, imazalil, imibenconazole, iprobenfos, iprodione, isoprothiolane, KNF 317, copper compounds, such as Cu oxychloride, oxine-Cu, Cu oxide, mancozeb, maneb, mepanipyrim (KIM 3535), metconazol, mepronil, metalaxyl, methasulfocarb, methfuroxam, MON 24000, myclobutanil, nabam, nitrothalidopropyl, nuarimol, ofurace, oxadixyl, oxycarboxin, penconazole, pencycuron, PP 969, probenazole, propineb, prochloraz, procymidon, propamocarb, propiconazole, prothiocarb, pyracarbolid, pyrazophos, pyrifenox, pyrimethanil, pyroquilon, rabenzazole, RH7592, sulfur, tebuconazole, TF 167, thiabendazole, thicyofen, thiofanatemethyl, thiram, tolclofos-methyl, tolylfluanid, triadimefon, triadimenol, triazoxid, tricyclazole, tridemorph, triflumizol, triforine, triflonazol, validamycin, vinchlozolin, XRD 563, zineb, sodium dodecylsulfonate, sodium dodecyl sulfate, sodium C13/C15-alcohol ether-sulfonate, sodium cetostearyl phosphate ester, dioctyl sodium sulfosuccinate, sodium isopropyl-naphthalenesulfonate, sodium methylenebisnaphthalene-sulfonate, cetyl-trimethyl-ammonium chloride, salts of long-chain primary, secondary or tertiary amines, alkyl-propyleneamines, lauryl-pyrimidinium bromide, ethoxylated quaternized fatty amines, alkyl-dimethyl-benzyl-ammonium chloride and 1-hydroxyethyl-2-alkyl-imidazoline.

The above-mentioned combination partners are known active compounds, most of which are described in Ch.R Worthing, S. B. Walker, The Pesticide Manual, 7th Edition (1983), British Crop Protection Council, incorporated herein by reference. The active compound content of the use forms prepared from the commercially available formulations can vary within wide limits and the active compound concentration of the use forms can be from 0.0001 to 95% by weight of active compound, preferably between 0.0001 and 1% by weight. They are used in a customary manner appropriate for the use forms.

The present invention is further described and illustrated in the following examples. Further objects of this invention, together with additional features contributing thereto and advantages accruing therefrom, will be apparent from the following examples of the invention. It will be appreciated that variations and modifications in the embodiments described can be made by the skilled person without departing from the spirit or scope of the invention as defined in the appended claims.

A. FORMULATION EXAMPLES a) A dusting powder is obtained by mixing 10 parts by weight of active compound and 90 parts by weight of talc, as the inert substance, and comminuting the mixture in an impact mill.

b) A wettable powder which is readily dispersible in water is obtained by mixing 25 parts by weight of active compound, 65 parts by weight of kaolin-containing quartz, as the inert substance, 10 parts by weight of potassium ligninsulfonate and 1 part by weight of sodium oleoylmethyltauride, as the wetting and dispersing agent, and grinding the mixture in a pinned disk mill.

c) A dispersion concentrate which is readily dispersible in water is prepared by mixing 40 parts by weight of active compound with 7 parts by weight of a sulfosuccinic acid half-ester, 2 parts by weight of a sodium ligninsulfonate and 51 parts by weight of water and grinding the mixture to a fineness of less than 5 microns in a grinding bead mill.

d) An emulsifiable concentrate can be prepared from 15 parts by weight of active compound, 75 parts by weight of cyclohexane, as the solvent, and 10 parts by weight of oxyethylated nonylphenol (10 EO), as the emulsifier.

e) Granules can be prepared from 2 to 15 parts by weight of active compound and an inert granule carrier material, such as attapulgite, pumice granules and/or quartz sand. A suspension of the wettable powder from Example b) having a solids content of 30% is expediently used, and this is sprayed onto the surface of attapulgite granules and the components are dried and mixed intimately. The weight content of the wettable powder here is about 5% and that of the inert carrier material is about 95% of the finished granules.

B. PREPARATION EXAMPLES

Example A

5-Chloro-6-ethyl-4-[2-(4-methylphenyl)-1,3-dioxan-5-ylamino]-pyrimidine

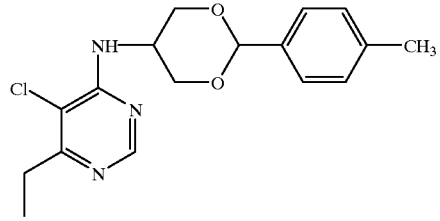

4.6 g (0.02 mol) of 5-chloro-6-ethyl-4-(1,3-dihydroxy-2-propylamino)-pyrimidine, 4.6 g (0.02 mol) of p-tolylaldehyde and 0.5 g of p-toluenesulfonic acid hydrate were heated in 100 ml of toluene for 6 hours using a water separator.

After cooling, the mixture was extracted by stirring with dilute sodium hydroxide solution and concentrated aqueous bisulfite solution and the organic phase was dried and concentrated. For purification and for separation of the cis/trans isomers, the residue was chromatographed over silica gel with ethyl acetate/petroleum ether (8:2). This gave initially 0.64 g (9.6% of theory) of the trans isomer (colorless crystals, melting point 129–130° C.), and then 3.55 g (53.2% of theory) of the cis isomer (colorless crystals, melting point 107–108° C.).

Preparation of the starting substance 5-chloro-6-ethyl-4-(1,3-dihydroxy-2-propylamino)-pyrimidine.

27.3 g (0.3 mol) of 2-amino-1,3-propanediol, 53.1 g (0.3 mol) of 4,5-dichloro-6-ethylpyrimidine and 44.6 g (0.45 mol) of triethylainine were heated under reflux in 500 ml of toluene for 6 hours. A white precipitate of triethylamine hydrochloride and undissolved product formed. The toluene was stripped off, the solid contents of the flask were dissolved in methanol and, for purification and removal of the triethylamine hydrochloride, the solution was chromatographed over silica gel with methanol as the mobile phase. This gave 39.0 g of colorless crystals (56.1% of theory), melting point 104–105° C.

Example B

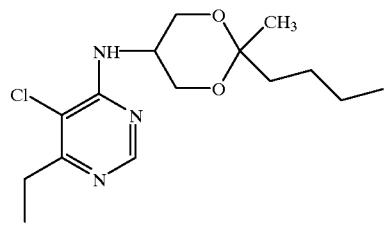

4-(2-n-Butyl-2-methyl-1,3-dioxan-5-ylamino)-5-chloro-6-ethyl-pyrimidine 2.16 g (9 mmol) of 5-chloro-6-ethyl-4-(1,3-dihydroxy-2-propylamino)-pyrimidine (Example 1), 1.80 g (18 mmol) of 2-hexanone and 500 mg of p-toluenesulfonic acid were heated in 100 ml of toluene for 8 hours, using a water separator. After the mixture had been extracted by stirring with dilute sodium hydroxide solution, the organic phase was dried and concentrated. The cis/trans isomers were separated by chromatography over silica gel (mobile phase: ethyl acetate/petroleum ether 4:1). 0.29 g of trans isomer (10.3% of theory, colorless oil) was first eluted, followed by 0.49 g of the cis isomer (17.3% of theory, colorless oil).

Example C

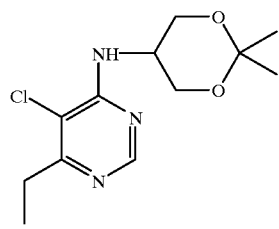

5-Chloro-6-ethyl-4-(2,2-dimethyl-1,3-dioxan-5-ylamino)-pyrimidine 2.65 g (15 mmol) of 4,5-dichloro-6-ethyl-pyrimidine, 2.40 g (18.3 mmol) of 5-amino-2,4-dimethyl-1,3-dioxane and 3.03 g (30 mmol) of triethylamine were heated under reflux in 10 ml of toluene for 4 hours. After cooling, the mixture was extracted by stirring with water and the organic phase was dried and concentrated. For purification, the residue was chromatographed over silica gel (ethyl acetate/petroleum ether 4:1). This gave 0.46 g (11% of theory) of product as a colorless oil.

Preparation of the precursor 2,2-dimethyl-1,3-dioxan-5-ylamine 6.1 g (47 mmol) of 2,2-dimethyl-1,3-dioxan-5-one (D. Enders, B. Bockstiegel, Synthesis 1989, 493, incorporated herein by reference) were subjected to reductive amination in 50 ml of ammonia—saturated methanol in an autoclave at 50° C. under a hydrogen pressure of 100 bar, using Raney nickel as the catalyst. After the catalyst had been filtered off and the filtrate concentrated, 4.8 g of a brown oil were obtained, this being further reacted without purification.

Example D

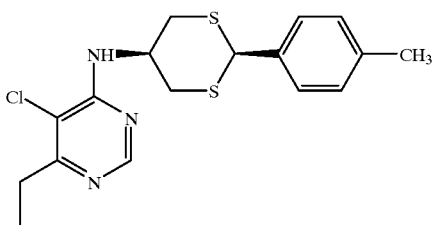

5-Chloro-6-ethyl-4-[cis-2-(4-methylphenyl)-1,3-dithian-5-ylamino]-pyrimidine 1.77 g (10 mmol) of 4,5-dichloro-6-ethyl-pyrimidine and 2.2 g (10 mmol) of 5-amino-2-(4-methylphenyl)-1,3-dithian were stirred with 2.02 g of triethylamine at 80–90° C. for 6 hours. The mixture was taken up in water/methylene chloride and the organic phase was dried and concentrated. For purification, the residue was chromatographed over silica gel (eluting agent petroleum ether/ethyl acetate 4:1). This gave 1.0 g of colorless solid (27.3% of theory), melting point: 138–139° C.

Preparation of the educt 5-amino-2-(4-methylphenyl)-1,3-dithian 22.4 g (0.1 mol) of 2-(4-methylphenyl)-1,3-dithian-5-one and 77.1 g (1.0 mol) of ammonium acetate were stirred in 250 ml of methanol with the addition of 37.5 g of molecular sieve (3 Å) for 30 minutes and 6.30 g (0.1 mol) of sodium cyanoborohydride were then added in portions at 20° C. The mixture was stirred at room temperature for 48 hours, diluted with methanol and filtered. The filtrate was concentrated and the residue was taken up in dilute hydrochloric acid/toluene. The hydrochloric acid phase was rendered basic with concentrated sodium hydroxide solution and extracted with ether. This gave 2.2 g of product as a colorless oil (9.8% of theory), which was reacted without further purification.

Preparation of 2-(4-methylphenyl)-1,3-dithian-5-one 131 g of methyl 2-(4-methylphenyl)-1,3-dithia-cyclohexan-5-one-4-carboxylate (0.464 mol) were heated under reflux with 350 ml of 2N sulfuric acid for 6 hours, with intensive stirring. After cooling, the mixture was decanted and the residue was taken up in ethyl acetate. The organic phase was washed with bicarbonate solution and water, dried and concentrated. For further purification, the solid residue was suspended in diisopropyl ether and filtered off with suction. This gave 62.7 g of yellow crystals (60.2% of theory), melting point: 112–113° C.

Preparation of methyl 2-(4-methylphenyl)-1,3-dithian-5-one-4-carboxylate 42.30 g of sodium hydride (80% dispersion in oil) (1.41 mol) were suspended in 700 ml of toluene and the suspension was heated to 90° C. 211.2 g (0.67 mol) of bis-(5-carbomethoxymethyl)-(4-methylbenzaldehyde)-mercaptal were slowly added dropwise at this temperature. Severe evolution of hydrogen and a yellow coloration of the reaction mixture occurred. If necessary, it was possible to start the reaction by addition of a few drops of ethanol. The mixture was then stirred at 100° C. for 4 hours. After cooling to room temperature, 20 ml of ethanol were added dropwise to destroy excess sodium hydride, water was added, the mixture was brought to pH 3 with concentrated hydrochloric acid and the organic phase was separated off. The aqueous phase was extracted twice more by stirring with toluene and the combined organic phases were extracted by stirring with bicarbonate solution. After drying and concentration of the organic phase, 131.7 g of product (69.4% of theory) were obtained, this being reacted without further purification.

Preparation of bis-(5-carbomethoxymethyl)-(4-methylphenyl)-mercaptal 120.1 g (1.0 mol) of p-tolylaldehyde and 201.7 g (1.9 mol) of methyl mercaptoacetate were heated with 5 g of p-toluenesulfonic acid hydrate in 600 ml of toluene, using a water separator, until the formation of water had ended. The mixture was then extracted twice by stirring with bicarbonate solution and water and the organic phase was dried and concentrated. To remove excess aldehyde, the crude product was dissolved in ethyl acetate and extracted by stirring with concentrated sodium bisulfite solution. After drying and concentration of the organic phase, 213.2 g of crude product were obtained (67.8% of theory), this being reacted further without further purification.

Example E

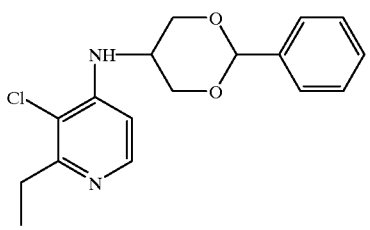

3-Chloro-2-ethyl-4-(2-phenyl-1,3-dioxan-5-ylamino)-pyridine 2.3 g (10 mmol) of 5-chloro-6-ethyl-4-(1,3-dihydroxy-2-propylamino)-pyridine (prepared analogously to Example A from 2-amino-1,3-propanediol and 3,4-dichloro-2-ethyl-pyridine) and 5.0 g of benzaldehyde were heated with 2.1 g of p-toluenesulfonic acid hydrate in 40 ml of toluene, using a water separator, until the evolution of water had ended. Working up and purification were carried out analogously to Example A. the chromatography over silica gel (ethyl acetate) gave initially 0.6 g of trans isomer (18.8% of theory), melting point: 139–140° C., and then 2.4 g of cis isomer (75.2% of theory), melting point 119–120° C.

Example F

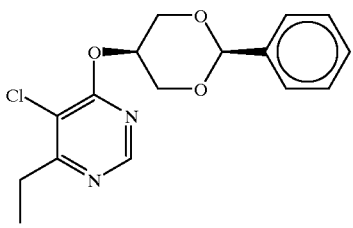

5-Chloro-6-ethyl-4-(cis-2-phenyl-dioxan-5-yloxy)-pyrimidine 1.8 g (10 mmol) of cis-5-hydroxy-2-phenyl-1,3-dioxane (E. Juaristi, S. Antunez, Tetrahedron 48, 5941 (1992), incorporated herein by reference) and 1.8 g of 4,5-dichloro-6-ethyl-pyrimidine were initially introduced into 15 ml of dry tetrahydrofuran, and 0.4 g (12 mmol) of sodium hydride (80% in mineral oil) was added in portions at room temperature. The mixture was subsequently stirred at room temperature for 8 hours, 2 ml of methanol were added dropwise and the mixture was concentrated. The residue was taken up in ethyl acetate, the mixture was filtered and the filtrate was concentrated. For purification, the residue was chromatographed over silica gel (petroleum ether/ethyl acetate 1:1).

This gave 1.0 g (31.2% of theory) of colorless solid. Melting point 114–115° C.

Example G

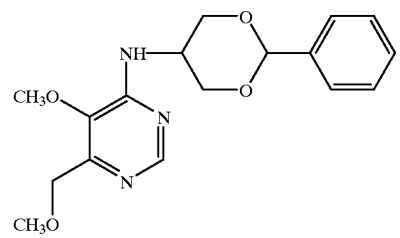

5-Methoxy-6-methoxymethyl-4-(2-phenyl-1,3-dioxan-5-ylamino)-pyrimidine

In analogy to example A there was first synthesized the intermediate 4-(1,3-dihydroxy-2-propylamino)-5-methoxy-6-methoxy-methyl-pyrimidine-[4-chloro-5-methoxy-6-methoxymethylpyrimidine (Collection Czechosl. Chem. Commun. 33 (1968) 2266), 2-amino-1,3-propanediol, triethylamine, toluene as solvent; yellow oil; NMR (CDCl$_3$, 300 Mhz) $\bar{o}$=3,47 (s, 3H, OCH$_3$), 3,48 (s, 2H, OH), 3,80 (s, 3H, OCH$_3$), 3,88 (m, 4H, CH$_2$), 4,11 (m, 1H, CH), 4,44 (s, 2H, CH$_2$), 6,04 (d, 1H, NH), 8,26 (s, 1H, CH) which was subsequently converted to the target compound by reaction with benzaldehyde in the presence of p-toluenesulfonic acid hydrate and toluene as solvent. Chromatography over silica gel (ethyl acetate/methanol 9:1) gave initially the trans isomer (yellow oil), NMR (CDCl$_3$, 200 Mhz), $\bar{o}$=3,50 (s, 3H, OCH$_3$), 3,70 (tr, 2H, dioxan-H), 3,80 (s, 3H, OCH$_3$), 4,45 (dd, 2H, dioxan-H), 4,50 (s, 2H, CH$_2$), 4,60 (m, 1H, CH), 5,05 (d, 1H, NH), 5,55 (s, 1H, ketal-H), 7,30–7,55 (2m, 5H, phenyl-H), 8,40 (s, 1H, pyrimidine-H) and then the cis isomer (yellow oil, NMR (CDCl$_3$), 200 Mhz); $\bar{o}$=3,50 (s, 3H, OCH$_3$), 3,85 (s, 3H, OCH$_3$), 4,20–4,30 (m, s, 5H, dioxan-H), 4,50 (s, 2H, CH$_2$), 5,65 (s, 1H, ketal-H), 6,15 (d, 1H, NH), 7,35–7,55 (2m, 5H, phenyl-H), 8,35 (s, 1H, pyrimidine-H).

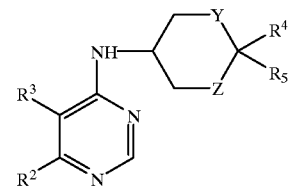

| Ex. No. | $R^2$ | $R^3$ | $R^4$ | $R^5$ | Isomer | Y | Z | m.p. [° C.] |
|---|---|---|---|---|---|---|---|---|
| 1 | C$_2$H$_5$ | Cl | H | Phenyl | trans | O | O | 117–118 |
| 2 | " | " | " | " | cis | " | " | 83–84 |
| 3 | " | " | CH$_3$ | " | trans | " | " | |
| 4 | " | " | " | " | cis | " | " | |
| 5 | " | " | H | 4-Chlor-phenyl | trans | " | " | 142–143 |
| 6 | " | " | " | " | cis | " | " | 87–88 |
| 7 | " | " | " | 4-Fluor-phenyl | cis | " | " | 82–84 |
| 8 | " | " | " | 4-Brom-phenyl | trans | " | " | |

-continued

| Ex. No. | R² | R³ | R⁴ | R⁵ | Isomer | Y | Z | m.p. [° C.] |
|---|---|---|---|---|---|---|---|---|
| 9 | " | " | " | " | cis | " | " | |
| 10 | " | " | " | 4-Jod-phenyl | trans | " | " | |
| 11 | " | " | " | " | cis | " | " | |
| 2 | " | " | " | 4-Methyl-phenyl | trans | " | " | 129–130 |
| 13 | " | " | " | " | cis | " | " | 107–108 |
| 14 | " | " | CH₃ | 4-Methyl-phenyl | trans | " | " | oil |
| 15 | " | " | " | " | cis | " | " | oil |
| 16 | " | " | H | 4-Ethyl-phenyl | trans | " | " | 103–105 |
| 17 | " | " | " | " | cis | " | " | 73–75 |
| 18 | " | " | " | 4-n-Propyl-phenyl | trans | " | " | |
| 19 | C₂H₅ | Cl | H | 4-n-Propyl-phenyl | cis | O | O | |
| 20 | " | " | " | 4-Isopropyl-phenyl | trans | " | " | |
| 21 | " | " | " | " | cis | " | " | 95–96 |
| 22 | " | " | " | 4-n-Butyl-phenyl | trans | " | " | 86–87 |
| 23 | " | " | " | " | cis | " | " | 71–72 |
| 24 | " | " | " | 4-Iso-butyl-phenyl | trans | " | " | 74–75 |
| 25 | " | " | " | 4-Iso-butyl-phenyl | cis | " | " | 76–77 |
| 26 | " | " | " | 4-tert.-Butyl-phenyl | cis | " | " | 99–100 |
| 27 | " | " | " | 4-n-Octyl-phenyl | trans | " | " | |
| 28 | " | " | " | " | cis | " | " | |
| 29 | " | " | " | 4-Trifluor-methylphenyl | trans | " | " | 133–134 |
| 30 | " | " | " | 4-Trifluor-methylphenyl | cis | " | " | 80–81 |
| 31 | " | " | " | 4-Methoxy-phenyl | trans | " | " | |
| 32 | " | " | " | " | cis | " | " | |
| 33 | " | " | " | 4-Difluor-methoxyphenyl | trans | " | " | 94–95 |
| 34 | " | " | " | 4-Difluor-methoxyphenyl | cis | " | " | 84–85 |
| 35 | " | " | " | 4-Trifluor-methoxyphenyl | cis | " | " | 61–62 |
| 36 | " | " | " | 4-Ethoxyphenyl | cis | " | " | 131–132 |
| 37 | C₂H₅ | Cl | H | 4-tert.-Butoxy-phenyl | trans | O | O | |
| 38 | " | " | " | 4-tert.-Butoxy-phenyl | cis | " | " | 112–113 |
| 39 | " | " | " | 4-Biphenyl | trans | " | " | 155–156 |
| 40 | " | " | " | " | cis | " | " | 138–140 |
| 41 | " | " | " | 1-Naphthyl | trans | " | " | |
| 42 | " | " | " | " | cis | " | " | |
| 43 | " | " | " | 2-Naphthyl | trans | " | " | 138–140 |
| 44 | " | " | " | " | cis | " | " | 105–107 |
| 45 | " | " | " | 2,4-Difluor-phenyl | trans | " | " | 141–142 |
| 46 | " | " | " | 2,4-Difluor-phenyl | cis | " | " | 75–76 |
| 47 | " | " | " | 2,6-Difluor-phenyl | trans | " | " | 158–159 |
| 48 | " | " | " | 2,6-Difluor-phenyl | cis | " | " | 123–124 |
| 49 | " | " | " | 4-Chlor-3-trifluor-methylphenyl | trans | " | " | 91–93 |
| 50 | " | " | " | 4-Chlor-3-trifluor-methylphenyl | cis | " | " | 104–105 |
| 51 | " | " | " | 3,4-Dimethoxy-phenyl | trans | " | " | 111–112 |
| 52 | " | " | " | 3,4-Dimethoxy-phenyl | cis | " | " | 88–89 |
| 53 | " | " | " | 3,4-Methylen-dioxyphenyl | cis | " | " | 128–129 |
| 54 | C₂H₅ | Cl | H | 3,4-Ethylen-dioxyphenyl | cis | O | O | 119–120 |
| 55 | " | " | " | 3,4-Methylen-dioxy-5-methoxyphgenyl | cis | " | " | 113–115 |
| 56 | " | " | " | 2-Thienyl | trans | " | " | 82–83 |
| 57 | " | " | " | " | cis | " | " | 76–77 |
| 58 | " | " | " | 2-Methyl-thien-5-yl | trans | " | " | |
| 59 | " | " | " | " | cis | " | " | 120–121 |
| 60 | " | " | " | 4-Methyl-thien-2-yl | trans | " | " | |
| 61 | " | " | " | 4-Methyl-thien-2-yl | cis | " | " | |
| 62 | " | " | " | 4-Brom-thien-2-yl | trans | " | " | 83–85 |
| 63 | " | " | " | " | cis | " | " | 92–94 |
| 64 | " | " | " | 2-Brom-thien-5-yl | trans | " | " | |

-continued

| Ex. No. | R² | R³ | R⁴ | R⁵ | Isomer | Y | Z | m.p. [° C.] |
|---|---|---|---|---|---|---|---|---|
| 65 | " | " | " | " | cis | " | " | |
| 66 | " | " | " | 2-Chlor-thien-5-yl | trans | " | " | |
| 67 | " | " | " | " | cis | " | " | |
| 68 | " | " | " | 2-Ethyl-thien-5-yl | trans | " | " | |
| 69 | " | " | " | " | cis | " | " | |
| 70 | " | " | " | Thiazol-2-yl | trans | " | " | 193–194 |
| 71 | C₂H₅ | Cl | H | Thiazol-2-yl | cis | O | O | liquid |
| 72 | " | " | " | 2-Pyridyl | trans | " | " | |
| 73 | " | " | " | " | cis | " | " | |
| 74 | " | " | " | 3-Pyridyl | trans | " | " | |
| 75 | " | " | " | " | cis | " | " | |
| 76 | " | " | " | 4-Pyridyl | trans | " | " | |
| 77 | " | " | " | " | cis | " | " | |
| 78 | " | " | CH₃ | CH₃ | — | " | " | oil |
| 79 | CH₂OCH₃ | OCH₃ | " | " | — | " | " | |
| 80 | C₂H₅ | Cl | H | n-C₃H₇ | cis | " | " | |
| 81 | " | " | " | i-C₃H₇ | " | " | " | |
| 82 | " | " | " | n-C₄H₉ | " | " | " | oil |
| 83 | " | " | " | tert.-C₄H₉ | " | " | " | 55–56 |
| 84 | " | " | " | n-C₈H₁₇ | " | " | " | |
| 85 | " | " | " | Cyclohexyl | " | " | " | oil |
| 86 | " | " | " | 1-Phenylethyl | " | " | " | oil |
| 87 | " | " | " | 2-Phenyl-ethyl | " | " | " | oil |
| 88 | " | " | " | 3-(4-Iso-propylphenyl)-2-methylpropyl | " | " | " | |
| 89 | " | " | " | 3-(4-tert.-Butylphenyl-2-methylpropyl | " | " | " | |
| 90 | C₂H₅ | Cl | CH₃ | n-C₄H₉ | trans | O | O | oil |
| 91 | " | " | " | " | cis | " | " | oil |
| 92 | C₂H₅ | Cl | —(CH₂)₄— | | — | O | O | oil |
| 93 | " | " | —(CH₂)₂—CHC₆H₅—(CH₂)₂— | | — | " | " | |
| 94 | " | " | H | p-Tolyl | cis | S | S | 138–139 |
| 95 | " | " | H | 3,4-(2,2-Difluor-methylendioxy)-phenyl | cis | O | O | |
| 96 | C₂H₅ | Cl | H | 4-Methylthio-phenyl | cis | O | O | oil |
| 97 | " | " | " | 4-Methylthio-phenyl | trans | " | " | 126–127 |
| 98 | C₂H₅ | Cl | H | 4-Ethylthiophenyl | cis | O | O | |
| 99 | " | " | " | 4-Propylthio-phenyl | cis | " | " | |
| 100 | " | " | " | 4-Isopropylthio-phenyl | cis | " | " | 85 86 |
| 101 | " | " | " | 4-Isopropylthio-phenyl | trans | " | " | 104–105 |
| 102 | " | " | " | 4-tert.-Butylthio-phenyl | cis | " | " | 153–154 |
| 103 | " | " | " | 4-tert.-Butylthio-phenyl | trans | " | " | 126–127 |
| 104 | " | " | " | 3-Flour-4-methyl-thiophenyl | cis | " | " | 77–78 |
| 105 | " | " | " | 3-Fluor-4-methyl-thiophenyl | trans | " | " | 147–148 |
| 106 | " | " | " | 3-Chlor-4-methyl-thiophenyl | cis | " | " | 68–69 |
| 107 | " | " | " | 3-Chlor-4-methyl-thiophenyl | trans | " | " | 133–134 |
| 108 | " | " | " | 3-Brom-4-methyl-thiophenyl | cis | " | " | 81–82 |
| 109 | " | " | " | 3-Brom-4-methyl-thiophenyl | trans | " | " | 140–141 |
| 110 | " | " | " | 4-Methylsulfinyl-phenyl | cis | " | " | 149–151 |
| 111 | " | " | " | 4-Methylsulfonyl-phenyl | cis | " | " | 158–160 |
| 112 | " | " | " | 3-Methyl-4-methylthio-phenyl | " | " | " | |
| 113 | " | " | " | 3-Thienyl | cis | " | " | 95–97 |
| 114 | " | " | " | " | trans | " | " | |
| 115 | " | " | " | 3-Methyl-thien-2-yl | cis | " | " | oil |
| 116 | " | " | " | " | trans | " | " | oil |
| 117 | " | " | " | 3-Brom-thien-2-yl | cis | " | " | |

-continued

| Ex. No. | R² | R³ | R⁴ | R⁵ | Isomer | Y | Z | m.p. [° C.] |
|---|---|---|---|---|---|---|---|---|
| 118 | " | " | " | " | trans | " | " | |
| 119 | C₂H₅ | Cl | H | 5-Methoxy-thien-2-yl | cis | O | O | |
| 120 | " | " | " | " | trans | O | O | |

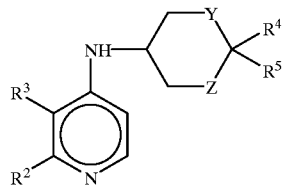

| Ex. No. | R² | R³ | R⁴ | R⁵ | Isomer | Y | Z | m.p. [° C.] |
|---|---|---|---|---|---|---|---|---|
| 150 | C₂H₅ | Cl | H | Phenyl | trans | O | O | 139–140 |
| 151 | " | " | " | " | cis | " | " | 119–120 |
| 152 | " | " | " | 4-Chlorphenyl | trans | " | " | |
| 153 | " | " | " | " | cis | " | " | |
| 154 | " | " | " | 4-Fluorphenyl | trans | " | " | |
| 155 | " | " | " | " | cis | " | " | |
| 156 | " | " | " | 4-Bromphenyl | trans | " | " | 162–163 |
| 157 | " | " | " | " | cis | " | " | 120–121 |
| 158 | " | " | " | 2-Fluorphenyl | trans | " | " | |
| 159 | " | " | " | " | cis | " | " | |
| 160 | " | " | " | 3-Methoxy-phenyl | trans | " | " | 121–122 |
| 161 | " | " | " | " | cis | " | " | 121–122 |
| 162 | " | " | " | 2,4-Dimethoxy-phenyl | trans | " | " | 138–139 |
| 163 | " | " | " | " | cis | " | " | |
| 164 | " | " | " | 2,3-Dimethoxy-phenyl | trans | " | " | |
| 165 | " | " | " | " | cis | " | " | 97–98 |
| 166 | " | " | " | 2,5-Dimethoxy-phenyl | trans | " | " | 114–115 |
| 167 | C₂H₅ | Cl | H | 2,5-Dimethoxy-phenyl | cis | O | O | |
| 168 | " | " | " | 4-n-Octyloxy-phenyl | trans | " | " | |
| 169 | " | " | " | " | cis | " | " | 66–67 |
| 170 | " | " | " | 3-Phenoxy-phenyl | trans | " | " | |
| 171 | " | " | " | " | cis | " | " | |
| 172 | " | " | " | 4-Trifluor-methoxyphenyl | trans | " | " | |
| 173 | " | " | " | " | cis | " | " | |
| 174 | " | " | " | 1-Naphthyl | trans | " | " | |
| 175 | " | " | " | " | cis | " | " | |
| 176 | " | " | " | 2-Brom-3-methoxy-pyridin-4-yl | trans | " | " | |
| 177 | " | " | " | " | cis | " | " | |
| 178 | " | " | " | tert.-Butyl | trans | " | " | 123–124 |
| 179 | " | " | " | " | cis | " | " | 86–87 |
| 180 | " | " | " | n-Undecyl | trans | " | " | |
| 181 | " | " | " | " | cis | " | " | 54–55 |
| 182 | " | " | " | 4-Methylphenyl | cis | " | " | |

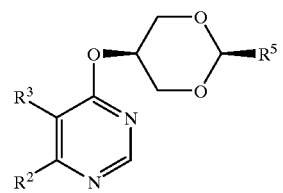

| Ex. No. | R² | R³ | R⁵ | M.p. [° C.] |
|---|---|---|---|---|
| 200 | C₂H₅ | Cl | Phenyl | 114–115 |
| 201 | CH₂OCH₃ | OCH₃ | Phenyl | 112–113 |
| 202 | —CH=CH—CH=CH— | | Phenyl | 193–195 |
| 203 | —(CH₂)4— | | Phenyl | |
| 204 | C₂H₅ | Cl | 4-Methylphenyl | |

All the examples listed in the above tables with the 5-chloro-6-ethyl-pyrimidine system can be prepared completely analogously, for example, with the 5-chloro-6-methyl-, 5-bromo-6-ethyl- or the 5-methoxy-6-methoxymethyl-pyrimidine system or the quinazoline or 8-fluoro-quinazoline system.

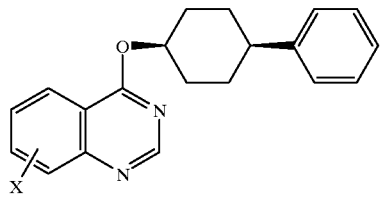

| Ex. No. | X | m.P. [° C.] |
|---|---|---|
| 205 | 7-Cl | 165–168 |
| 206 | 2-CCl$_3$ | 129–132 |
| 207 | 2-CHCl$_2$ | 176–179 |
| 208 | 5-Cl | 246 (decomp.) |
| 209 | 6-CH$_3$ | 200–202 |
| 210 | 8-Cl | 155–157 |
| 211 | 8-F | 134–136 |
| 212 | 6-F | 218–220 |
| 213 | 8-CH$_3$ | 151–153 |
| 214 | 6,7-(OCH$_3$)$_2$ | 222–223 |
| 215 | 6-Cl | 206–207 |

BIOLOGICAL EXAMPLES

Use as a Fungicide

The activity of the preparations according to the invention was evaluated in accordance with a scale of 0–4, where
0 is 0–24% suppression of infestation
1 is 25–49% suppression of infestation
2 is 50–74% suppression of infestation
3 is 75–97% suppression of infestation
4 is 97–100% suppression of infestation.

Example A

Barley plants of the "Maris Otter" variety were sprayed in the 2-leaf stage with a solution of the compounds according to the invention in a mixture of 40% of acetone and 60% of water until dripping wet. 24 hours later, the plants were inoculated with conidia of powdery mildew of barley (Erysiphe graminis f. sp. hordei) and were kept in a climatically controlled chamber at 20° C. and a relative atmospheric humidity of 75–80%. 7 days after the treatment, the plants were investigated for infestation with powdery mildew of barley.

The following compounds were evaluated with 3 or 4 at 50 mg of active compound/l of spray liquor:
Compounds according to Examples No. 2, 5, 7, 13, 23, 26, 30, 35, 38, 40, 53, 62, 86, 202 and 211.

Example B

Tomato plants of the variety "First in the Field" were sprayed in the 3- to 4-leaf stage with a solution of the compounds according to the invention in a mixture of 40% of acetone and 60% of water until dripping wet. 24 hours later, the plants were inoculated with a spore suspension of Phytophthora infestans (20 000 spores/ml) and kept in a climatically controlled chamber at 15° C., first for 2 days at 99% relative atmospheric humidity and then for 4 days at 75–80% relative atmospheric humidity. 6 days after the treatment, the plants were investigated for infestation with Phytophthora infestans. The following compounds were rated with 3 or 4 at 50 mg of active substance/l of spray liquor:
Compounds according to Examples No. 2, 13, 23, 35, 38, 53, 54, 85 and 86.

Example C

Seedlings of the grape variety "Gruiner Veltliner" about 6 weeks old were sprayed with a solution of the compounds according to the invention in a mixture of 40% of acetone and 60% of water until dripping wet. 24 hours later, the plants were inoculated by spraying with a zoospore suspension (100 000/ml) of Plasmopara viticola and kept in a climatically controlled chamber at 70° C. and a relative atmospheric humidity of about 99%. 14 days after treatment, the plants were investigated for their infestation with Plasmopara viticola.

The following compounds were rated with 3 or 4 at 50 mg of active substance/l of spray liquor:
Compounds according to Examples No. 2, 5, 26, 37, 38, 40, 52, 53, 62 and 83.

Example D

Wheat plants of the variety "Hornet" were sprayed in the 2-leaf stage with a solution of the compounds according to the invention in a mixture of 40% of acetone and 60% of water until dripping wet. 24 hours later, the plants were inoculated by spraying with a pycniospore suspension (500 000/ml) of Leptosphaeria nodorum and kept in a climatically controlled chamber at 18–20° C. and a relative atmospheric humidity of about 99%. 14 days after inoculation, the plants were investigated for their infestation with Leptosphaeria nodorum.

The following compounds were rated with 3 or 4 at 50 mg of active substance/l of spray liquor:
Compounds according to Examples No 5, 22, 23, 57, 36, 37, 38 and 182.

Example E

Rice plants of the variety "Nihonbare" were sprayed in the 1.5-leaf stage with a solution of the compounds according to the invention in a mixture of 40% of acetone and 60% of water until dripping wet. At the same time, a solution of the substances in a mixture of 5% of acetone and 95% of water was applied by watering. 24 hours later, the plants were inoculated by spraying with a pycniospore suspension ($10^6$/ml) of Pyricularia oryzae. The plants were kept in a darkened climatically controlled chamber at 26° C. and a relative atmospheric humidity of 99% for 2 days and then transferred to an illuminated climatically controlled chamber at about 18° C. and a relative atmospheric humidity of 75–80%. 7–9 days after inoculation, the plants were investigated for their infestation with Pyricularia oryzae.

The following substances were rated with 3 or 4 at 50 mg of active substance/l of spray liquor:
Compounds according to Examples No. 2, 5, 7, 13, 17, 25, 36, 38, 43, 44, 62, 91, 96, 102, 105, 182 and 202.

Example F

Apple seedlings (Malus sp.) about 3 weeks old were sprayed with a solution of the compounds according to the invention in a mixture of 40% of acetone and 60% of water until dripping wet. After 24 hours, the plants were inoculated by spraying with a spore suspension (300 000/ml) of Venturia inaequalis. The plants were kept in the dark at 18–20° C. and a relative atmospheric humidity of 99% for 2 days, and then in the light at the same atmospheric humidity for 5 days, and finally at 75–80% atmospheric humidity for 7 days. 14 days after treatment, the plants were investigated for their infestation with Venturia inaequalis.

The following substances were rated with 3 or 4 at 50 mg of active substance/l of spray liquor:

Compounds according to Examples No. 25, 35 and 57.

Example G

Tomato plants of the variety "First in the Field" were sprayed in the 2- to 3-leaf stage with a solution of the compounds according to the invention in a mixture of 40% of acetone and 60% of water until dripping wet. After 24 hours, the plants were inoculated with a spore suspension (500 000/ml) of Botrytis cinerea. The plants were kept in a climatically controlled chamber at 18–20° C. and 99% relative atmospheric humidity. 5 days after inoculation, the plants were investigated for their infestation with Botrytis cinerea.

The following substances were rated with 3 or 4 at 50 mg of active substance/l of spray liquor:

Compounds according to Examples No. 54, 85 and 86.

Use as an Insecticide/Acaricide

Example A

In each case 1 ml of the formulation tested, emulsified in water, was applied uniformly to the inside of the lid and the base of a Petri dish, and after the deposit dried, in each case 10 imagos of the housefly (Musca domestica) were introduced. After the dishes were closed, they were kept at room temperature, and the mortality of the test animals was determined after 3 hours. At 250 ppm (based on the content of active compound), the preparations according to Examples No. 2, 6, 7, 33, 35, 36, 40, 49, 50, 52, 53, 54, 55, 57, 85, 94, 101 and 115 showed a 100% mortality of the test animals employed.

Example B

Rice seed was germinated under damp conditions on cotton-wool in growing glasses and, after growing to a stem length of about 8 cm, the leaves were introduced into the test solution to be tested. After the solution dripped off, the rice plants treated in this way were introduced into cultivation containers, separated according to the test concentration, and infested with in each case 10 larvae (L3) of the species Nilaparvata lugens. After the closed cultivation containers were kept at 21° C., the mortality of the leafhopper larvae could be determined after 4 days. At a concentration of 250 ppm (based on the content of active compound), the preparations according to Examples No. 2, 6, 7, 13, 23, 26, 29, 33, 35, 36, 40, 46, 48, 49, 50, 53, 54, 57, 85, 86 and 94 showed a 100% mortality of the test animals employed.

Example C

Wheat seed was pregerminated under water for 6 hours and then placed in 10 ml glass test tubes and covered in each case with 2 ml of soil. After addition of 1 ml of water, the plants remained in the cultivation glasses at room temperature (21° C.) until a growth height of about 3 cm was reached. Middle Diabrotica undecimpunctata larvae stages (in each case 10) were then placed on the soil in the glasses and, after 2 hours, 1 ml of the test liquid in the concentration to be tested was pipetted onto the soil surface in the glasses. After the glasses stood under laboratory conditions (21° C.) for 5 days, the soil and the root parts were examined for live Diabrotica larvae and the mortality was determined. At 250 ppm (based on the content of active compound), the preparations according to Examples No. 2, 6, 7, 13, 26, 29, 33, 36, 38, 40, 52, 53, 54, 57, 85, 86, 92, 94, 101, 127 and 129 showed a 100% mortality of the test animals employed.

Example D

Broad beans (Vicia faba) heavily infested with the black bean aphid (Aphis fabae) were sprayed with aqueous dilutions of wettable powder concentrates having an active compound content of 250 ppm up until the stage where they started to drip. The mortality of the aphids was determined after 3 days. 100% destruction was achieved with the compounds according to Examples No. 2, 6, 7, 12, 13, 23, 26, 29, 33, 35, 36, 38, 40, 48, 50, 52, 53, 54, 57, 85, 86 and 92.

Example E

Bean plants (Phaseolus v.) heavily infested with two-spotted spider mites (Tetranychus urticae, full population) were sprayed with an aqueous dilution of a wettable powder concentrate which comprised 250 ppm of the particular active compound. The mortality of the mites was checked after 7 days. 100% destruction was achieved with the compounds according to Examples No. 2, 6, 7, 13, 23, 26, 29, 33, 35, 36, 38, 39, 40, 48, 50, 53, 54, 55, 57, 85, 86 and 94.

Example F

Disks of filter paper on which eggs of cotton stainers (Oncopeltus fasciatus) lay were treated with in each case 0.5 ml of an aqueous dilution of the formulation to be tested. After the deposit dried on, the Petri dish was closed and the inside was kept at maximum atmospheric humidity. After the dish had been kept at room temperature, the ovicidal action was determined after 7 days. With an active compound content of 500 ppm, a 100% ovicidal action was achieved with the compounds according to Examples No. 6, 13, 33, 35, 48, 52, 53, 54, 55, 57, 85, 86, 94, 101 and 115.

Example G

Leaves of the Phaseolus vulgaris bean were covered uniformly with eggs of the whitefly (Trialeurodes vaporariorum) and, after a development time of the whitefly population to the L2–L3 stage, were sprayed uniformly with the aqueous test emulsions of the formulation. After 4 days, a microscopic check of the larvae on the leaves showed that a 100% destruction was achieved with the compounds according to Examples No. 6, 7, 13, 26, 35, 36, 48, 52, 53, 54, 57 and 86.

Example H

L2 larvae of Spodoptera litoralis (Egyptian cotton-worm) were placed in Petri dishes which were covered with filter paper on the base and which contained a small amount of nutrient medium. The base with the nutrient medium and the larvae on top was sprayed with the aqueous emulsions of the test substances and the Petri dishes were closed with a lid. After 5 days at about 23° C., the action of the compounds on the larvae was determined. It was found that with the method mentioned, a 100% action was achieved on Spodoptera litoralis larvae with the compounds according to Examples No. 13, 29 and 33 at a concentration of the spray liquor of 250 ppm (based on the active compound).

Example J
Control of Root Gall Nematodes

An aqueous formulation comprising 0.03% of active compound was prepared in a glass vessel (final volume 20 ml). About 5000 freshly hatched, active (mobile) larvae (2nd development stage) of root gall nematodes (Meloidogyne incognita) were added to this prepared mixture. After 6 days of continuous exposure of the nematode larvae, the percentage proportion of individuals which became motionless (immobile) due to the action of the active compound was determined in comparison with the untreated controls. This percentage proportion is called percent nematicidal contact action (Test Section A).

After conclusion of this test section, the entire solution (active compound and pretreated nematode larvae) was poured into a pot with three pre-cultivated cucumber plants (Cucumis stivus; soil volume 60 ml; age of the cucumber plants: 9 days after sowing). As a result of this drench application, the active compound content was reduced to 0.009%, based on the soil volume. The host plants treated in this way were then cultivated further in a greenhouse (25 to 27° C., watering twice daily). After two weeks, the host plants with the root balls were removed from the soil mixture infested with nematodes and freed from adhering soil. The plant growth and root formation of the host plants were evaluated visually during this procedure, and recorded. The number of root galls per plant was then counted and compared with the infestation of untreated control plants. The calculation of the percentage reduction in infestation as a criterion for evaluation of the action was carried out in accordance with the Abbott formula. The result is called the percent nematicidal soil drench action (Test Section B).

The compounds of Examples 2, 6, 7, 13, 35, 57, 83, 87, 96, 110 and 111 showed a 90 to 100% action against the root gall nematode Meloidogyne incognita in Test Section A and Test Section B.

Use as an Antiparasitic

Example A

In vitro test on tropical cattle ticks (Boophilus microplus)

It was possible to detect the activity of the compounds according to the invention against ticks in the following experimental arrangement:

To prepare a suitable active compound formulation, the active compounds were dissolved to the extent of 10% (w/v) in a mixture comprising dimethylformamide (85 g), nonylphenol polyglycol ether (3 g) and ethoxylated castor oil (7 g), and the emulsion concentrates thus obtained were diluted with water to a test concentration of 500 ppm.

In each case ten fully satiated females of the tropical tick Boophilus microplus were dipped in these active compound dilutions for five minutes. The ticks were then dried on filter paper and then attached with their back to an adhesive film for the purpose of oviposition. The ticks were kept in a heated cabinet at 28° C. and an atmospheric humidity of 90%.

As a control, tick females were dipped only in water. Two weeks after the treatment, the inhibition of oviposition was used to evaluate the activity.

In this test, the compounds according to Examples No. 2, 7, 13, 17, 21, 23, 25, 26, 33, 35, 36, 38, 40, 44, 50, 52, 54, 55, 57, 63, 85, 87, 96, 100, 104, 106, 108, 110, 111, 179 and 182 in each case caused 100% inhibition of the laying of eggs.

The above description of the invention is intended to be illustrative and not limiting. Various changes or modifications in the embodiments described may occur to those skilled in the art. These can be made without departing from the spirit or scope of the invention.

What is claimed is:

1. A compound of the formula I

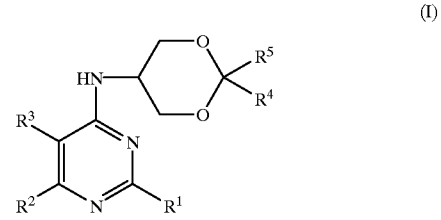

in which $R^1$ is hydrogen, halogen, $(C_1-C_4)$-alkyl, $(C_1-C_4)$-haloalkyl or $(C_3-C_5)$-cycloalkyl;

$R^2$ and $R^3$ are identical or different and are each hydrogen, $(C_1-C_4)$-alkyl, $(C_1-C_4)$-haloalkyl, $(C_2-C_4)$-alkenyl, $(C_2-C_4)$-haloalkenyl, $(C_2-C_4)$-alkynyl, $(C_2-C_4)$-haloalkynyl, $(C_1-C_8)$-trialkylsilylalkynyl, phenyl-$(C_1-C_8)$-dialkyl-silyl-alkynyl, aryl-$(C_1-C_2)$-alkyl-$(C_1-C_8)$-dialkyl-silyl-alkynyl, $(C_3-C_8)$-cycloalkyl-$(C_1-C_8)$-dialkyl-silyl-alkynyl, (1-methyl-sila-$(C_3-C_8)$-cycloalkyl-1-yl)-alkynyl, triphenylsilylalkynyl, $(C_1-C_4)$-alkoxy, $(C_1-C_4)$-haloalkoxy, $(C_1-C_4)$-alkoxy-$(C_1-C_4)$-alkyl, $(C_1-C_4)$-haloalkoxy-$(C_1-C_4)$-alkyl, $(C_1-C_4)$-alkoxy-$(C_1-C_4)$-haloalkyl, $(C_1-C_4)$-haloalkoxy-$(C_1-C_4)$-haloalkyl, halogen, hydroxyl, $(C_1-C_4)$-hydroxyalkyl, $(C_1-C_4)$-alkanoyl, $(C_1-C_4)$-alkanoyl-$(C_1-C_4)$-alkyl, $(C_1-C_4)$-haloalkanoyl, $(C_3-C_5)$-cycloalkyl, $(C_3-C_5)$-halocycloalkyl, cyano, $(C_1-C_4)$-cyanoalkyl, nitro, $(C_1-C_4)$-nitroalkyl, thiocyano, $(C_1-C_4)$-thiocyanoalkyl, $(C_1-C_4)$-alkoxycarbonyl, $(C_1-C_4)$-alkoxycarbonyl-$(C_1-C_4)$-alkyl, $(C_1-C_4)$-haloalkoxycarbonyl, $(C_1-C_4)$-alkylthio, $(C_1-C_4)$-alkylthio-$(C_1-C_4)$-alkyl, $(C_1-C_4)$-haloalkylthio, $(C_1-C_4)$-alkylsulfinyl, $(C_1-C_4)$-haloalkylsulfinyl, $(C_1-C_4)$-alkylsulfonyl or $(C_1-C_4)$-haloalkylsulfonyl; or $R^2$ and $R^3$, together with the carbon atoms to which they are bonded, form an unsaturated 5- or 6-membered isocyclic ring which, if it is a 5-membered ring, optionally contains one oxygen or sulfur atom instead of $CH_2$ or which, if it is a 6-membered ring, optionally contains one or two nitrogen atoms instead of one or two CH units, and which is optionally substituted by 1, 2 or 3 identical or different radicals, and these radicals are $(C_1-C_4)$-alkyl, $(C_1-C_4)$-haloalkyl, halogen, $(C_1-C_4)$-alkoxy or $(C_1-C_4)$-haloalkoxy; or $R^2$ and $R^3$, together with the carbon atoms to which they are bonded, form a saturated 5-, 6- or 7-membered isocyclic ring which optionally contains oxygen and/or sulfur instead of one or two $CH_2$ groups, and which is optionally substituted by 1, 2 or 3 $(C_1-C_4)$-alkyl groups;

$R^4$ and $R^5$ are substituents of the heteroaliphatic ring system;

$R^4$ is hydrogen, halogen, $(C_1-C_4)$-alkyl, $(C_1-C_4)$-haloalkyl, $(C_1-C_4)$-alkoxy or $(C_1-C_4)$-alkylthio;

$R^5$ is alkyl, alkenyl, alkynyl, aryl or heterocyclyl, where the aryl or heterocyclyl radicals mentioned are unsubstituted or provided with up to three, in the case of fluorine also up to the maximum number of, identical or different radicals, and in the alkyl, alkenyl or alkynyl radicals mentioned, one or more non-adjacent saturated carbon units are optionally replaced by a carbonyl group or by oxygen, $S(O)_x$, where x=0, 1 or 2, $NR^6$ or $SiR^7R^8$, in which $R^6$ is hydrogen, $(C_1-C_4)$-alkyl, $(C_1-C_4)$-alkoxy or $(C_1-C_4)$-alkanoyl and $R^7$ and $R^8$ are $(C_1-C_4)$-alkyl; and wherein, furthermore, 3 to 12 atoms of these hydrocarbon radicals optionally modified as above can form a ring, and these hydrocarbon radicals, with or without the variations mentioned, are optionally substituted by one or more identical or different radicals from the group consisting of halogen, aryl, aryloxy, arylthio, cycloalkoxy, cycloalkylthio, heterocyclyl, heterocyclyloxy, heterocyclylthio, alkanoyl, cycloalkanoyl, haloalkanoyl, aroyl, arylalkanoyl, cycloalkylalkanoyl, heterocyclylalkanoyl, alkoxycarbonyl, haloalkoxycarbonyl, cycloalkoxycarbonyl, cycloalkylalkoxycarbonyl, arylalkoxycarbonyl, heterocyclylalkoxycarbonyl, aryloxycarbonyl, heterocyclyloxycarbonyl, alkanoyloxy, haloalkanoyloxy, cycloalkanoyloxy, cycloalkylalkanoyloxy, aroyloxy, arylalkanoyloxy, heterocycloylalkanoyloxy, alkylsulfonyloxy, arylsulfonyloxy, hydroxyl, cyano, thiocyano and nitro, where the cycloaliphatic, aromatic or heterocyclic ring systems among the substituents just mentioned are unsubstituted or provided with up to three, in the case of fluorine also up to the maximum number of, identical or different substituents or a salt thereof.

2. A compound of the formula I as claimed in claim 1, in which $R^5$ is $(C_1-C_{20})$-alkyl, $(C_2-C_{20})$-alkenyl, $(C_2-C_{20})$-alkynyl, aryl or heterocyclyl, where the aryl or heterocyclyl radicals mentioned are unsubstituted or provided with up to three, in the case of fluorine also up to the maximum number of, identical or different radicals, and in the alkyl, alkenyl or alkynyl radicals mentioned, one or more non-adjacent saturated carbon units are optionally replaced by a carbonyl group or by oxygen, $S(O)_x$, where x=0, 1 or 2, $NR^6$ or $SiR^7R^8$, in which $R^6$ is hydrogen, $(C_1-C_4)$-alkyl, $(C_1-C_4)$-alkoxy or $(C_1-C_4)$-alkanoyl and $R^7$ and $R^8$ are $(C_1-C_4)$-alkyl, and wherein, furthermore, 3 to 12 atoms of these hydrocarbon radicals optionally modified as above optionally form a ring, and these hydrocarbon radicals, with or without the variations mentioned, are optionally be substituted by one or more identical or different radicals from the group consisting of halogen, aryl, aryloxy, arylthio, $(C_3-C_8)$-cycloalkoxy, $(C_3-C_8)$-cycloalkylthio, heterocyclyl, heterocyclyloxy, heterocyclylthio, $(C_1-C_{12})$-alkanoyl, $(C_3-C_8)$-cycloalkanoyl, $(C_2-C_{12})$-haloalkanoyl, aroyl, aryl-$(C_1-C_4)$-alkanoyl, $(C_3-C_8)$-cycloalkyl-$(C_1-C_4)$-alkanoyl, heterocyclyl-$(C_1-C_4)$-alkanoyl, $(C_1-C_{12})$-alkoxycarbonyl, $(C_1-C_{12})$-haloalkoxycarbonyl, $(C_3-C_8)$-cycloalkoxycarbonyl, $(C_3-C_8)$-cycloalkyl-$(C_1-C_4)$-alkoxycarbonyl, aryl-$(C_1-C_4)$-alkoxycarbonyl, heterocyclyl-$(C_1-C_4)$-alkoxycarbonyl, aryloxycarbonyl, heterocyclyloxycarbonyl, $(C_1-C_{12})$-alkanoyloxy, $(C_2-C_{12})$-haloalkanoylalkoxy, $(C_3-C_8)$-cycloalkanoyloxy, $(C_3-C_8)$-cycloalkyl-$(C_1-C_4)$-alkanoyloxy, aroyloxy, aryl-$(C_1-C_4)$-alkanoyloxy, heterocyclyl-$(C_1-C_4)$-alkanoyloxy, $(C_1-C_{12})$-alkylsulfonyloxy, arylsulfonyloxy, hydroxyl, cyano, thiocyano and nitro, where the cycloaliphatic, aromatic or heterocyclic ring systems among the substituents just mentioned are unsubstituted or provided with up to three, in the case of fluorine also up to the maximum number of, identical or different substituents, or a salt thereof.

3. A compound of the formula I as claimed in claim 1, in which $R^1$ is hydrogen or fluorine;

$R^2$ and $R^3$ are hydrogen, $(C_1-C_4)$-alkyl, $(C_2-C_4)$-alkenyl, $(C_2-C_4)$-alkynyl, trimethylsilylethynyl, methoxycarbonyl, $(C_1-C_4)$-haloalkyl, halogen, methoxymethyl or cyano; or $R^2$ and $R^3$, together with the carbon atoms to which they are bonded, form an optionally substituted unsaturated 5- or 6-membered ring which, in the case of the 5-membered ring, optionally contains one sulfur atom instead of one $CH_2$ unit; or $R^2$ and $R^3$, together with the carbon atoms to which they are bonded, form a saturated 5- or 6-membered ring which optionally contains one sulfur or one oxygen atom instead of one $CH_2$ unit;

$R^4$ is hydrogen, $(C_1-C_4)$-alkyl, trifluoromethyl or $(C_1-C_4)$-alkoxy;

or a salt thereof.

4. A compound of the formula I as claimed in claim 1, in which $R^1$ is hydrogen, $R^2$ and $R^3$ are hydrogen, methyl, ethyl, propyl, $(C_2-C_3)$-alkenyl, $(C_2-C_3)$-chloro- or fluoro-alkenyl, $(C_2-C_3)$-alkynyl, trimethylsilylethynyl, $(C_1-C_3)$-chloro- or fluoroalkyl, methoxymethyl, halogen or cyano, $R^2$ and $R^3$, together with the ring system to which they are bonded, form the quinazoline or quinoline system which is optionally substituted by fluorine in the carbocyclic part; or $R^2$ and $R^3$, together with the carbon atoms to which they are bonded, form a saturated 6-membered ring which optionally contains one oxygen or sulfur atom instead of one $CH_2$ group;

$R^4$ is hydrogen or methyl;

or a salt thereof.

5. A compound of the formula I as claimed in claim 1, in which $R^1$ is hydrogen;

$R^2$ is methyl, ethyl, propyl, isopropyl, vinyl, ethynyl, $(C_1-C_2)$-fluoroalkyl or methoxymethyl;

$R^3$ is fluorine, chlorine, bromine, cyano, vinyl, ethynyl, $(C_1-C_2)$-fluoroalkyl or methoxy; or $R^2$ and $R^3$, together with the ring system to which they are bonded, form the quinazoline system which can be substituted by a fluorine atom;

$R^4$ is hydrogen, or a salt thereof.

6. A compound of the formula I as claimed in claim 1, in which $R^5$ is $(C_1-C_{15})$-alkyl, aryl or heterocyclyl in the sense of a heteroaromatic ring system, where the aryl or heterocyclyl radical are unsubstituted or provided with up to three, in the case of fluorine also up to the maximum number of, identical or different radicals, and in the alkyl radical mentioned, one or more non-adjacent saturated carbon units can be replaced by oxygen, and wherein, furthermore, 3 to 8 atoms of this alkyl radical optionally modified as above can form a ring, and this alkyl radical, with or without the variations mentioned, can optionally be substituted by one or more halogen atoms, in the case of fluorine also up to the maximum number, or by an aryl radical, and this aryl radical are unsubstituted or provided with up to three, in the case of fluorine also up to the maximum number of, identical or different substituents, or a salt thereof.

7. A compound of the formula I as claimed in claim 1, in which, in the case where $R^4$ is hydrogen, the substituents NH and $R^5$ are in the cis-position relative to one another, or a salt thereof.

8. An insecticidal, acaricidal, ixodicidal, nematicidal, fungicidal, or pharmaceutical composition comprising an active amount of at least one compound as claimed in claim 1 and with an additive or auxiliary.

9. A method of controlling harmful insects, Acarina, mollusks or nematodes, in which an active amount of a compound as claimed in claim 1 is applied to such insects, Acarina, mollusks or nematodes or to the plants, areas or substrates infested by them.

10. A method of controlling endo- or ectoparasites in animals, which comprises administration of an amount of a compound as claimed in claim 1 active for its use to said animals.

11. A method for controlling phytopathogenic fungi, which comprises applying a fungicidally effective amount of a compound according to claim 1 or to the fungi, or to plants, area or substrates infested by said fungi.

12. A compound of the formula I as claimed in claim 1, in which
  $R^1$ is hydrogen;
  $R^2$ is ethyl or methoxymethyl;
  $R^3$ is chlorine, bromine or methoxy;
  $R^4$ is hydrogen;
  $R^5$ is $(C_1-C_{20})$-alkyl, $(C_2-C_{20})$-alkenyl, $(C_2-C_{20})$-alkynyl, aryl or heterocyclyl, where the aryl or heterocyclyl radicals mentioned are unsubstituted or provided with up to three, in the case of fluorine also up to the maximum number of, identical or different radicals, and in the alkyl, alkenyl or alkynyl radicals mentioned, one or more non-adjacent saturated carbon units are optionally replaced by oxygen or $SiR^7R^8$, in which $R^7$ and $R^8$ are $(C_1-C_4)$-alkyl,
    and wherein, furthermore, 3 to 6 atoms of these hydrocarbon radicals optionally modified as above optionally form a ring, and these hydrocarbon radicals, with or without the variations mentioned, are optionally be substituted by one or more identical or different radicals from the series consisting of halogen, aryl, aryloxy, arylthio, $(C_3-C_8)$-cycloalkoxy, $(C_3-C_8)$-cycloalkylthio, heterocyclyl, heterocyclyloxy and $(C_1-C_2)$-alkoxycarbonyl, where the cycloaliphatic, aromatic or heterocyclic ring systems among the substituents just mentioned can be unsubstituted or provided with up to three, in the case of fluorine also up to the maximum number of, identical or different substituents, or a salt thereof.

13. The compound of the formula I as claimed in claim 12, wherein $R^2$ is ethyl and $R^3$ is chlorine.

\* \* \* \* \*